(12) United States Patent
Lambert et al.

(10) Patent No.: US 8,507,206 B2
(45) Date of Patent: Aug. 13, 2013

(54) MONOCLONAL ANTIBODIES THAT TARGET PATHOLOGICAL ASSEMBLIES OF AMYLOID β (ABETA)

(75) Inventors: Mary P Lambert, Glenview, IL (US); Pauline T. Velasco, Wilmette, IL (US); Lei Chang, Westmont, IL (US); Kirsten L. Viola, Chicago, IL (US); Sara J. Fernandez, Chicago, IL (US); Pascale N. Lacor, Chicago, IL (US); Daliya Khuon, Chicago, IL (US); Yuesong Gong, Evanston, IL (US); William L. Klein, Winnetka, IL (US); Grant A. Krafft, Glenview, IL (US)

(73) Assignees: Northwestern University, Evanston, IL (US); Acumen Pharmaceuticals, Inc., South San Francisco, CA (US)

( * ) Notice: Subject to any disclaimer, the term of this patent is extended or adjusted under 35 U.S.C. 154(b) by 1389 days.

(21) Appl. No.: 11/571,532

(22) PCT Filed: Jul. 5, 2005

(86) PCT No.: PCT/US2005/023958
§ 371 (c)(1), (2), (4) Date: Mar. 6, 2007

(87) PCT Pub. No.: WO2006/014478
PCT Pub. Date: Feb. 9, 2006

(65) Prior Publication Data
US 2007/0218499 A1    Sep. 20, 2007

Related U.S. Application Data

(60) Provisional application No. 60/585,318, filed on Jul. 2, 2004, provisional application No. 60/621,776, filed on Oct. 25, 2004.

(51) Int. Cl.
*G01N 33/53* (2006.01)
(52) U.S. Cl.
USPC ........................................ 435/7.1; 530/388.1
(58) Field of Classification Search
None
See application file for complete search history.

(56) References Cited

FOREIGN PATENT DOCUMENTS

| WO | WO 01/62801 A2 * | 8/2001 |
|---|---|---|
| WO | WO03104437 A2 | 12/2003 |
| WO | WO2004031400 A2 | 4/2004 |
| WO | WO2005011599 A2 | 2/2005 |
| WO | WO2005110056 A2 | 11/2005 |
| WO | WO2005110056 A3 | 11/2005 |

OTHER PUBLICATIONS

Howard and Bethell, Eds. Basic Methods in Antibody Production and Characterization. Edition: illustrated. CRC Press (Boca Raton), 2001, p. 52.*
Friedman et al. Soluble Protofibrils as Metastable Intermediates in Simulations of Amyloid Fibril Degradation Induced by Lipid Vesicles. J Phys Chem Lett 2010, 1: 471-474.*
Wu et al. Phenol red interacts with the protofibril-like oligomers of an amyloidogenic hexapeptide NFGAIL through both hydrophobic and aromatic contacts. Biophys J. Nov. 15, 2006;91(10):3664-72. Epub Aug. 25, 2006.*
Bacskai et al., Non-Fc-Mediated Mechanisms Are Involved in Clearance of Amyloid-Beta in Vivo by Immunotherapy, The Journal of Neuroscience 2002 22(18):7873-7878.
Bard et al., "Epitope and isotype specificities of antibodies of Beta-amyloid peptide for protection against Alzheimer's disease-like neuropathology", Proc Natl Acad Sci USA 2003 100(4):2023-2028.
Bard et al., "Peripherally administered antibodies against amyloid Beta-peptide enter the central nervous system and reduce pathology in a mouse model of Alzheimer's disease", Nature Medicine 2000 6(8):916-919.
Chang et al., "Femtomole Immunodetection of Synthetic and Endogenous Amyloid-Beta Oligomers and Its Application to Alzheimer's Disease Drug Candidate Screening", Journal of Molecular Neuroscience 2003 20:305-313.
Hock et al., "Antibodies against Beta-Amyloid Slow Cognitive Decline in Alzheimer's Disease", Neuron 2003 38:547-554.
Kotilineck et al., "Reversible Memory Loss in a Mouse Transgenic Model of Alzheimer's Disease", The Journal of Neuroscience 2002 22(15):6331-6335.
Lambert et al., "Vaccination with soluble ABeta oligomers generates toxicity-neutralizing antibodies", Journal of Neurochemistry 2001 79:595-605.
Lambert et al., "ADDLs-generated monoclonal antibodies target epitopes specific to ABeta Oligomers", Snf 2003 Annual Conference, Poster #527.16.
McLaurin et al., "Therapeutically effective antibodies against amyloid-Beta peptide target amyloid-Beta residues 4-10 and inhibit cytotoxicity and fibrillogenesis", Nature Medicine 2002 8(11):1263-1269.

* cited by examiner

*Primary Examiner* — Gregory S Emch
(74) *Attorney, Agent, or Firm* — Licata & Tyrrell P.C.

(57) ABSTRACT

Disclosed herein are antibodies that bind with high specificity to soluble oligomers of amyloid β (Abeta) and methods of employing those antibodies. The antibodies are able to distinguish between Alzheimer's Disease (AD) and control human brain extracts. The antibodies identify endogenous Abeta oligomers in AD brain slices and also bind to Abeta oligomers on cultured hippocampal cells. The antibodies neutralize endogenous Abeta oligomers and Abeta oligomers produced in solution.

1 Claim, 24 Drawing Sheets

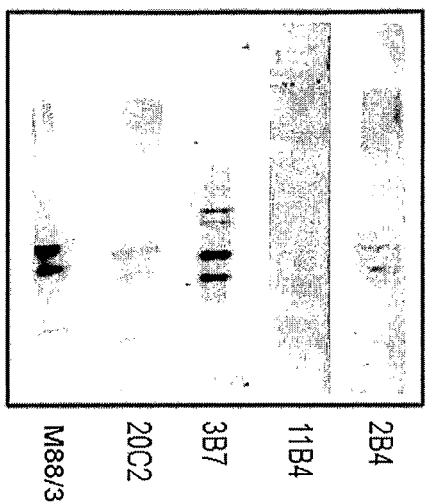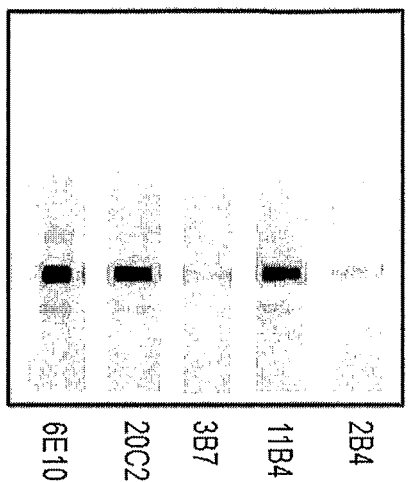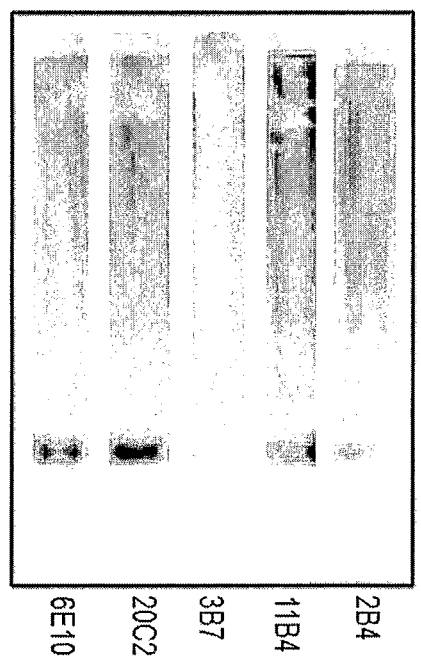
Fig. 8

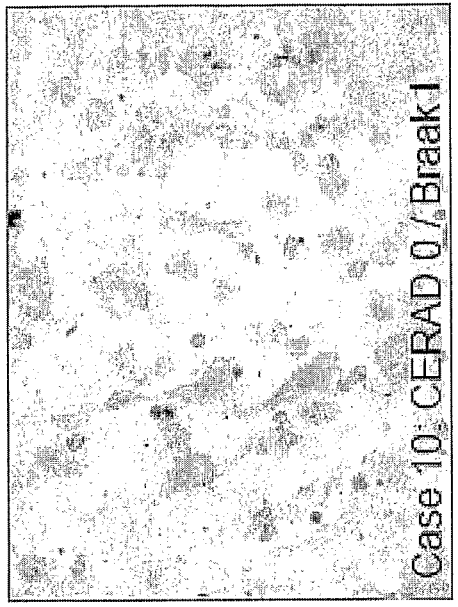

| Region | Case 16—CERAD A, Braak III, NIA/Reagan not classifiable | Case 28—CERAD C, Braak VI, NIA/Reagan high likelihood dementia due to AD |
|---|---|---|
| Entorhinal ctx | 0 | N/A |
| PHCG | ++ p-n & DP | +++ p-n, DP, NP, ++ AA |
| Temporooccipital | + p-n | +++ p-n, DP, NP, + AA |
| Hippocampus | ++ p-n & DP | +++ p-n, DP, NP ++AA |
| Subiculum | 0 | ++ p-n, DP, NP |
| Presubiculum | 0 | ++ p-n & DP |
| Amygdala | + p-n | + NP |
| MFG | ++ p-n & DP | +++ p-n, DP, NP, +AA |
| STG | ++ p-n, DP, NP | +++ p-n, DP, NP |
| IP | ++ p-n, DP, NP | +++ p-n, DP, NP |
| Motor | + p-n, DP, NP | ++ p-n, DP, NP |
| Sensory | + p-n & NP | + p-n & NP |
| Occipital | + NP | + NP |
| Globus pallidus | 0 | 0 |
| Putamen | 0 | + p-n & DP |
| Nbm | + p-n & DP | + p-n |
| Cbm | 0 | + meningeal vessels only |

Labeling patterns: p-n = peri-neuronal, CP = diffuse plaque-like, NP = neuritic plaque-like, AA = amyloid angiopathy

Fig. 13A

| Case | PMI | Age | Gender | Clinical Dx | Neuropath Dx | NP/DP sev. | CERAD (Thio-S) | Braak | NIA-Reagan |
|---|---|---|---|---|---|---|---|---|---|
| 1 | 9 | 53 | F | NND | No AD path. | 0/1 | 0 | 0 | N/A |
| 2 | 6 | 55 | F | NND | No AD path. | 0/0 | 0 | 0 | N/A |
| 3 | 5 | 56 | M | NND | No AD path. | 0/0 | 0 | 0 | N/A |
| 4 | 12 | 59 | M | NND | No AD path. | 0/0 | 0 | 0 | N/A |
| 5 | 8 | 63 | M | NND | No AD path. | 0/0 | 0 | 0 | N/A |
| 6 | 5 | 67 | F | NND | No AD path. | 0/0 | 0 | 0 | N/A |
| 7 | 6 | 68 | M | NND | No AD path. | 0/0 | 0 | 0 | N/A |
| 8 | 17 | 72 | F | NND | AD-aging | 0/1 | 0 | I | N/C |
| 9 | 8 | 61 | F | NND | AD-aging | 0/1 | 0 | I | N/C |
| 10 | 7 | 83 | F | NND | AD-aging | 0/0 | 0 | I | N/C |
| 11 | 5 | 53 | M | NND | AD-aging | 0/0 | 0 | I | N/C |
| 12 | 16 | 77 | M | NND | AD-aging | 0/0 | 0 | II | N/C |
| 13 | 3 | 70 | F | NND | AD-aging | 1/1 | A | II | low |
| 14 | 12 | 79 | F | NND | AD-aging | 1/1 | A | II | low |
| 15 | 6 | 64 | F | NND | AD-aging | 1/3 | B | II | low |
| 16 | 6 | 107 | F | NND | AD-aging | 1/2 | A | III | N/C |
| 17 | 6 | 89 | M | NND | AD-aging | 1/1 | B | 0 | N/C |
| 18 | 4 | 77 | M | NND | AD-aging | 2/1 | B | I | N/C |
| 19 | 3 | 78 | M | NND | AD-aging | 2/2 | B | III | N/C |
| 20 | 4 | 84 | M | NND | AD-aging | 2/2 | B | II | N/C |
| 21 | 15 | 83 | F | PRAD | Probable AD | 2/2 | B | V | N/C |
| 22 | 19 | 81 | M | VaD vs depr | Probable AD | 2/2 | B | V | N/C |
| 23 | 11 | 79 | F | PRAD | Definite AD | 3/3 | C | V | high |
| 24 | 10 | 81 | M | PRAD | Definite AD | 3/3 | C | V | high |
| 25 | 16 | 72 | F | PRAD | Definite AD | 3/3 | C | VI | high |
| 26 | 6 | 58 | M | NND | Definite AD | 3/3 | C | VI | high |
| 27 | 12 | 81 | F | PRAD | Definite AD | 3/3 | C | VI | high |
| 28 | mk | 76 | M | PRAD | Definite AD | 3/3 | C | VI | high |
| 29 | | 63 | F | PRAD | Definite AD | 3/3 | C | VI | high |

No or low pathology controls: cases 1–7
High pathology controls: cases 8–20
AD: cases 21–27
Avg. age 74, 15M, 14F

Fig. 14

|  | No to low-pathology controls Cases 1-13 | "High" pathology controls Cases 14-20 | AD cases Cases 21-29 |
|---|---|---|---|
| MFG | 0 to + p-n & DP | ++ to +++ p-n, DP, NP | +++ p-n, DP, NP |
| Hippocampus | 0 | 0 to ++ p-n | + to +++ NP, half + to +++ p-n |
| Subiculum | 0 | 0 to ++ p-n | 0 to +++ p-n, NP |
| Presubiculum | 0 | 0 to ++ p-n, 0 to +++ DP | ++ to +++ DP |
| Erc/PHCG | 0 (2 w + to ++ p-n, DP PHCG) | 0 to +++ p-n, DP, NP | ++ to +++p-n, DP, NP |
| Temporoocc. | 0 (2 with ++ p-n & DP) | + to ++ p-n, DP, NP | +++ p-n, DP, NP |

No to low-pathology controls: CERAD 0/Braak 0 to CERAD 0/Braak II, "High" pathology controls: CERAD B/Braak II, AD: CERAD B/Braak V to CERAD C/Braak VI ADDLs labeling similar to 4G8 and 1280

Fig. 16

| Case | Age | Gender | PMI | Clin Dx | Neuropath Dx | CERAD | Braak | NIA/Reagan | MFG | hippo | erc | transerc |
|---|---|---|---|---|---|---|---|---|---|---|---|---|
| 1 | 80 | M | 5 | NC | AD-aging | B | II | N/C | ++ | 0 | + | ++ |
| 2 | 89 | M | 5.3 | NC | Mild AD-aging | 0 | I | N/C | ++ | 0 | + | + |
| 3 | 95 | F | 13 | MCI | AD-aging | A | III | N/C | +++ | ++ | N/A | N/A |
| 4 | 90 | F | 3.8 | MCI | AD-aging | B | II | N/C | ++ | N/A | ++ | N/A |
| 5 | 87 | F | 18 | PRAD | AD | C | VI | high | +++ | +++ | N/A | N/A |
| 6 | 77 | F | 24 | POAD | AD | C | VI | high | +++ | +++ | N/A | N/A |

Fig. 17

Hippocampal cell culture ELISA shows ADDL binding that is concentration dependent

MONOCLONAL ANTIBODIES THAT TARGET PATHOLOGICAL ASSEMBLIES OF AMYLOID β (ABETA)

RELATED APPLICATIONS

This application claims priority from U.S. Patent App. No. 60/585,318, filed Jul. 2, 2004, and from U.S. Patent App. No. 60/621,776, filed Oct. 25, 2004.

STATEMENT OF GOVERNMENT SUPPORT

This invention was made with government support under Grant Numbers R01AG18877 and R01AG22547 awarded by the National Institutes of Health and Grant Number EEC-0118025 awarded by the National Science foundation (NSEC). The U.S. government has certain rights in the invention.

BACKGROUND

1. Field

The invention relates to the fields of biology and medicine. Specifically, the invention relates to the prevention, diagnosis, and treatment of neurodegenerative diseases, including, but not limited to, Alzheimer's disease.

2. Related Art

Alzheimer's disease (AD) is a progressive and degenerative dementia (Terry, R. D. et al. (1991) "Physical basis of cognitive alterations in Alzheimer's disease: synapse loss is the major correlate of cognitive impairment" Ann. Neurol., vol. 30, no. 4, pp. 572-580; Coyle, J. T. (1987) "Alzheimer's Disease" in Encyclopedia of Neuroscience, Ed. G. Adelman, pp 29-31, Birkhäuser: Boston-Basel-Stuttgart). In its early stages, however, AD manifests primarily as a profound inability to form new memories (Selkoe, D. J. (2002) "Alzheimer's disease is a synaptic failure" Science, vol. 298, pp. 789-791). The basis for this specific impact is not known, but evidence favors involvement of neurotoxins derived from amyloid beta (Aβ). Aβ is an amphipathic peptide whose abundance is increased by mutations and risk factors linked to AD. Fibrils formed from Aβ constitute the cores of amyloid plaques, which are hallmarks of AD brain. Analogous fibrils generated in vitro are lethal to cultured brain neurons. These findings provided the central rationale for the original amyloid cascade hypothesis, a remarkably productive theory in which memory loss was proposed to be the consequence of neuron death caused by fibrillar Aβ.

Despite its strong experimental support and intuitive appeal, the original amyloid cascade hypothesis has proven inconsistent with key observations, including the poor correlation between dementia and amyloid plaque burden (Katzman, R. (1988) "Clinical, pathological, and neurochemical changes in dementia: a subgroup with preserved mental status and numerous neocortical plaques" Ann. Neurol., vol. 23, no. 2, pp. 138-144). Particularly telling are recent studies of experimental AD vaccines done with transgenic hAPP mice (Dodart, J. C. et al. (2002) "Immunization reverses memory deficits without reducing brain Abeta burden in Alzheimer's disease model" Nat. Neurosci., vol. 5, pp. 452-457; Kotilinek, L. A. et al. (2002) "Reversible memory loss in a mouse transgenic model of Alzheimer's disease" J. Neurosci., vol. 22, pp. 6331-6335). These mice provide good models of early AD, developing age-dependent amyloid plaques and, most importantly, age-dependent memory dysfunction. Two surprising findings were obtained when mice were treated with monoclonal antibodies against Aβ: (1) vaccinated mice showed reversal of memory loss, with recovery evident in 24 hours; (2) cognitive benefits of vaccination accrued despite no change in plaque levels. Such findings are not consistent with a mechanism for memory loss dependent on neuron death caused by amyloid fibrils.

Salient flaws in the original hypothesis have been eliminated by an updated amyloid cascade that incorporates a role for additional neurologically active molecules formed by Aβ self-assembly. These molecules are soluble Aβ oligomers. Oligomers are metastable and form at low concentrations of Aβ1-42 (Lambert, M. P. et al. (1998) "Diffusible, nonfibrillar ligands derived from Abeta1-42 are potent central nervous system neurotoxins" Proc. Natl. Acad. Sci. USA, vol. 95, pp. 6448-6453). Essentially the missing links in the original cascade, Aβ oligomers rapidly inhibit long-term potentiation (LTP), a classic experimental paradigm for memory and synaptic plasticity. In the updated cascade: (1) memory loss stems from synapse failure, prior to neuron death; and (2) synapse failure is caused by Aβ oligomers, not fibrils (Hardy, J. & Selkoe, D. J. (2002) "The amyloid hypothesis of Alzheimer's disease: progress and problems on the road to therapeutics" Science, vol. 297, pp. 353-356). Recent reports show soluble oligomers occur in brain tissue and are strikingly elevated in AD (Kayed, R. et al. (2003) "Common structure of soluble amyloid oligomers implies common mechanism of pathogenesis" Science, vol. 300, pp. 486-489; Gong, Y. et al. (2003) "Alzheimer's disease-affected brain: presence of oligomeric Aβ ligands (ADDLs) suggests a molecular basis for reversible memory loss" Proc. Natl. Acad. Sci. USA, vol. 100, pp. 10417-10422) and in hAPP transgenic mice AD models (Kotilinek, L. A. et al. (2002) "Reversible memory loss in a mouse transgenic model of Alzheimer's disease" J. Neurosci., vol. 22, pp. 6331-6335; Chang, L. et al. (2003) "Femtomole immunodetection of synthetic and endogenous amyloid-β oligomers and its application to Alzheimer's Disease drug candidate screening" J. Mol. Neurosci., vol. 20, pp. 305-313).

Amyloid beta immunotherapy for Alzheimer's disease has shown initial success in mouse models of AD and in human patients not susceptible to meningoencephalitis. Disclosed herein are monoclonal antibodies against soluble Aβ oligomers (ADDLs). The antibodies distinguish between AD and control human brain extracts. The antibodies identify endogenous oligomers in AD brain slices and also bind to cultured hippocampal cells. The antibodies neutralize endogenous and "synthetic" ADDLs in solution. So-called "synthetic" ADDLs are produced in vitro by mixing purified amyloid β1-42 under conditions that produce ADDLs, see U.S. Pat. No. 6,218,506. One of the antibodies, 20C2, shows high selectivity for 3-24mers, but minimal detection of monomer Aβ peptides. Recognition of ADDLs by 20C2 is not blocked by short peptides that encompass the linear sequence of Aβ 1-42 or by Aβ 1-40. However, binding is blocked by Aβ 1-28, suggesting an epitope based on conformationally unique structures also attained with Aβ 1-28.

AD is a fatal progressive dementia that has no cure at present. Although the molecular basis of the disease is not established, considerable evidence indicates that it is a proteinopathy involving neurotoxins derived from the 42-amino acid peptide amyloid beta (Aβ). A recent revision of the major "amyloid cascade hypothesis" to explain disease progression states that small soluble Aβ oligomers, as well as the larger Aβ fibrils that constitute the core of plaques, are pathogenic (Hardy, J. & Selkoe, D. J. (2002) "The amyloid hypothesis of Alzheimer's disease: progress and problems on the road to therapeutics" Science, vol. 297, pp. 353-356).

Recent studies have shown that small soluble Aβ oligomers (also called Aβ-derived diffusible ligands or ADDLs) are present in AD brain, increasing up to 70-fold over control subjects (Gong, Y. et al. (2003) "Alzheimer's disease-affected brain: Presence of oligomeric Aβ ligands (ADDLs) suggests a molecular basis for reversible memory loss" Proc. Natl. Acad. Sci. USA, vol. 100, pp. 10417-10422). The very abundance of ADDLs in AD brain suggests their potential for therapeutic drugs or vaccines. Earlier clinical trials of a vaccine have revealed that persons mounting a vigorous immune response to the vaccine exhibited cognitive benefit (Hock, C. et al. (2003) "Antibodies against beta-amyloid slow cognitive decline in Alzheimer's disease" Neuron, vol. 38, pp. 547-554). These findings indicate genuine therapeutic promise, despite the unacceptable frequency of CNS inflammation that caused early termination of part of the trial (Birmingham, K. & Frantz, S. (2002) "Set back to Alzheimer vaccine studies" Nat. Med., vol. 8, pp. 199-200).

An alternative to a live vaccine is the development of therapeutic antibodies that target ADDLs without binding monomers or fibrils (Klein, W. L. (2002) "Aβ toxicity in Alzheimer's disease: globular oligomers (ADDLs) as new vaccine and drug targets" Neurochem. Int., vol. 41, pp. 345-352). Previous work has shown that ADDLs are excellent antigens, generating oligomer-selective polyclonal antibodies in rabbits at the very low antigen concentration of ~50 ug/ml (Lambert, M. P. et al. (2001) "Vaccination with soluble Abeta oligomers generates toxicity-neutralizing antibodies" J. Neurochem., vol. 79, pp. 595-605). Results from tg-mice models also suggest that antibodies can be successful in reversing memory decline (Dodart, J. C. et al. (2002) "Immunization reverses memory deficits without reducing brain Abeta burden in Alzheimer's disease" Nat. Neurosci., vol. 5, pp. 452-457).

Immunization of tg mice models of AD with fibrillar amyloid beta protein (Aβ) results in reduction of Aβ deposits in the brain and prevents the formation of this pathology when administered before its formation (Schenk, D. (2002) Amyloid-beta immunotherapy for Alzheimer's disease: the end of the beginning. Nat. Rev. Neurosci. 3(10):824-8; Schenk, D. et al. (1999) Immunization with amyloid-beta attenuates Alzheimer-disease-like pathology in the PDAPP mouse. Nature 400(6740):173-7). Learning and memory deficits produced in these mice are also reduced or prevented by similar active vaccination with preparations containing fibrillar Aβ (Janus, C. et al. (2000) A beta peptide immunization reduces behavioural impairment and plaques in a model of Alzheimer's disease. Nature 408(6815):979-82; Morgan, D. et al. (2000) A beta peptide vaccination prevents memory loss in an animal model of Alzheimer's disease. Nature 408(6815):982-5). Based on results from animal models, clinical trials were initiated and showed few adverse reactions in Phase 1. However, Phase 2 trials were halted when 6% of the patients developed meningoencephalitis (Birmingham, K. & Frantz, S. (2002) Set back to Alzheimer vaccine studies. Nat. Med. 8(3):199-200; Hock, C. et al. (2003) Antibodies against beta-amyloid slow cognitive decline in Alzheimer's disease. Neuron 38(4):547-54; Orgogozo, J. M. et al. (2003) Subacute meningoencephalitis in a subset of patients with AD after Abeta42 immunization. Neurology 61(1):46-54; Schenk, D. (2002) Amyloid-beta immunotherapy for Alzheimer's disease: the end of the beginning. Nat. Rev. Neurosci. 3(10):824-8; Schenk, D. et al. (2004) Current progress in beta-amyloid immunotherapy. Curr. Opin. Immunol. 16(5):599-606). Reports of the clinical outcome of these trials revealed that after 1 year patients producing antibodies that targeted plaques had a slower rate of cognitive decline than those patients that did not produce antibodies (Hock, C. et al. (2003) Antibodies against beta-amyloid slow cognitive decline in Alzheimer's disease. Neuron 38(4):547-54). Post mortem results on two patients showed absent or sparse plaques in the neocortex, with reactive microglia suggesting an effective immune response (Ferrer, I. et al. (2004) Neuropathology and pathogenesis of encephalitis following amyloid-beta immunization in Alzheimer's disease. Brain Pathol 14(1): 11-20; Nicoll, J. A. et al. (2003) Neuropathology of human Alzheimer disease after immunization with amyloid-beta peptide: a case report. Nat. Med. 9(4):448-52).

Alternative approaches to avoid inflammatory responses through the use of therapeutic antibodies are now under development (Agadjanyan, M. G. et al. (2005) Prototype Alzheimer's disease vaccine using the immunodominant B cell epitope from beta-amyloid and promiscuous T cell epitope pan HLA DR-binding peptide. J. Immunol. 174(3): 1580-6; Gelinas, D. S. et al. (2004) Immunotherapy for Alzheimer's disease. Proc. Natl. Acad. Sci. USA 101(Suppl 2):14657-62; Morgan, D. & Gitter, B. D. (2004) Evidence supporting a role for anti-Abeta antibodies in the treatment of Alzheimer's disease. Neurobiol. Aging 25(5):605-8; Schenk, D. et al. (2004) Current progress in beta-amyloid immunotherapy. Curr. Opin. Immunol. 16(5):599-606). It has been established that injections with Aβ-generated monoclonal antibodies produce cognitive improvement in tg mice models of AD. Using an antibody whose epitope targets the center of the Aβ peptide, it was shown that memory deficits can be reversed in PDAPP mice within 24 hours after treatment (Dodart, J. C. et al. (2002) Immunization reverses memory deficits without reducing brain A beta burden in Alzheimer's disease model. Nature Neuroscience 5(5):452-7). Similarly, in Tg2576 mice, memory loss was reversed using an antibody targeting the N-terminus of Aβ (Kotilinek, L. A. et al. (2002) Reversible memory loss in a mouse transgenic model of Alzheimer's disease. J. Neurosci. 22(15):6331-5).

Passive vaccination previously was shown to clear plaques from PDAPP and other tg mice models (Bacskai, B. J. et al. (2002) Non-Fc-mediated mechanisms are involved in clearance of amyloid-beta in vivo by immunotherapy. J. Neurosci. 22(18):7873-8; Bard, F. et al. (2003) Epitope and isotype specificities of antibodies to beta-amyloid peptide for protection against Alzheimer's disease-like neuropathology. Proc. Natl. Acad. Sci. USA 100(4):2023-8; Bard, F. et al. (2000) Peripherally administered antibodies against amyloid beta-peptide enter the central nervous system and reduce pathology in a mouse model of Alzheimer disease. Nat. Med. 6(8): 916-9; McLaurin, J. et al. (2002) Therapeutically effective antibodies against amyloid-beta peptide target amyloid-beta residues 4-10 and inhibit cytotoxicity and fibrillogenesis. Nature Medicine 8(11):1263-9). However, in the studies showing recovery from memory deficits, Aβ plaque burden was not decreased. A likely explanation for cognitive improvement without change in plaque burden is that these therapeutic antibodies immunoneutralize small, soluble oligomers of Aβ, which have been implicated in AD synapse failure (Lacor, P. N. et al. (2004) Synaptic targeting by Alzheimer's-related amyloid beta oligomers. J. Neurosci. 24(45): 10191-200). Aβ oligomers form at low doses of Aβ 1-42, block LTP, and specifically attach to synaptic terminals (Lacor, P. N. et al. (2004) Synaptic targeting by Alzheimer's-related amyloid beta oligomers. J. Neurosci. 24(45):10191-200; Lambert, M. P. et al. (1998) Diffusible, nonfibrillar ligands derived from Abeta1-42 are potent central nervous system neurotoxins. Proc. Natl. Acad. Sci. USA 95(11):6448-53; Wang, H. W. et al. (2002) Soluble oligomers of beta amyloid (1-42) inhibit long-term potentiation, but not long-term depression, in rat dentate gyrus. Brain Res. 924(2):133-40; Wang, Q. et al. (2004) Block of long-term potentiation by naturally secreted and synthetic amyloid beta-peptide in hippocampal slices is mediated via activation of the kinases c-Jun N-terminal kinase, cyclin-dependent kinase 5, and p38 mitogen-activated protein kinase as well as metabotropic glutamate receptor type 5. J. Neurosci. 24(13):3370-8). These oligomers (referred to as ADDLs) are elevated in AD brain and CSF and in tg mouse models (Chang, L. et al. (2003) Femtomole immunodetection of synthetic and endogenous amyloid-beta oligomers and its application to Alzheimer's disease drug candidate screening. J. Mol. Neurosci. 20(3): 305-13; Georganopoulou, D. G. et al. (2005) Nanoparticle-based detection in cerebral spinal fluid of a soluble pathogenic biomarker for Alzheimer's disease. Proc. Natl. Acad. Sci. USA 102(7):2273-76; Gong, Y. et al. Alzheimer's disease-affected brain: presence of oligomeric A beta ligands (ADDLs) suggests a molecular basis for reversible memory loss. Proc. Natl. Acad. Sci. USA 2003 100(18): 10417-22).

Given these considerations, oligomers provide an optimum target for therapeutic antibodies. The present invention addresses the need to obtain monoclonal antibodies selective for oligomers (ADDLs). The approaches disclosed herein use as antigen soluble Aβ oligomers (ADDLs) because of their previously demonstrated utility in providing epitopes dependent on quaternary structure in the generation of polyclonal antibodies. This strategy has generated monoclonal antibodies that distinguish between AD and control brains and that neutralize oligomers in solution, characteristics that will be essential for therapeutically useful antibodies.

BRIEF SUMMARY

In one embodiment, the invention comprises antibodies that bind soluble oligomers of amyloid β1-42. The oligomers can be ADDLs. The antibodies can be monoclonal. The antibodies can selectively bind oligomers (ADDLs) and not bind to amyloid β monomers or amyloid fibrils. As mentioned, the development and characterization of monoclonal antibodies that target epitopes specific to Aβ oligomers (ADDLs) are disclosed herein. Such antibodies can serve as human vaccines that can neutralize Aβ oligomers (ADDLs) without interference from plaque binding. Such antibodies can also serve as prototypes for such vaccines. Such vaccines can include humanized antibodies.

In another embodiment, the invention comprises methods for assaying soluble oligomers of amyloid β1-42 with monoclonal antibodies that do not bind amyloid β monomers or fibrils. The assaying can be qualitative or quantitative. The assaying can be in vitro, in vivo, or in vitro and in vivo. The assaying can be performed on samples isolated from patients or subjects. The assaying can detect compounds that interfere with the oligomers. The compounds can interfere with the assembly of the oligomers, with the activity of the oligomers, with the binding of the oligomers to their receptor(s), or with any combination thereof. The antibodies can be used to identify one or more cellular receptor(s) of the oligomers.

In another embodiment, the invention comprises compositions that comprise monoclonal antibodies that selectively bind to the oligomers. The compositions can be pharmaceutical compositions that are prepared, characterized, and used according to methods well known to persons skilled in the art. The compositions can be prophylactic, therapeutic, or prophylactic and therapeutic. The compositions can be administered to prevent neurodegenerative diseases or to treat neurodegenerative diseases. The diseases can be Alzheimer's disease (AD), mild cognitive impairment (MCI), Down's syndrome, and the like.

BRIEF DESCRIPTION OF THE DRAWINGS

FIG. 8: Binding profiles differ among selected Aβ antibodies. (Left, top) SDS-PAGE Western immunoblots using synthetic ADDLs at 20 pmol/lane were incubated with hybridoma supernates and visualized with appropriate HRP secondaries and chemiluminescence. Four profiles are illustrated: 1: Monomer, small molecular weight oligomers, and large molecular weight oligomers (20C2); 2: Small molecular weight oligomers (3B7); 3: Principle recognition of higher molecular weight oligomers (11B4); 4: Small and large molecular weight oligomers (2B4). The control is a polyclonal ADDL antibody, M88/3. (Right, top) A native Western immunoblot using synthetic ADDLs at 20 pmol/lane was prepared. The blot was then boiled for 5 min before visualization with the same hybridoma supernates. Supernates differ in their ability to recognize primary and peripheral non-denatured ADDL species. The control is 6E10 monoclonal antibody. (Bottom) A native Western immunoblot using synthetic ADDLs at 20 pmol/lane was prepared as above but not boiled. Supernatants recognize a primary lower molecular weight species and a smear of higher molecular weight species. 3B7 has little recognition of non-denatured material. Control is 6E10.

FIG. 14: Summary of IHC analyses using anti-ADDL monoclonal antibodies.

FIG. 16: Summary of ADDL IHC analyses with human brain sections.

FIG. 17: Results of ADDL IHC analyses on 6 cognitively evaluated cases.

DETAILED DESCRIPTION

Figure 1:
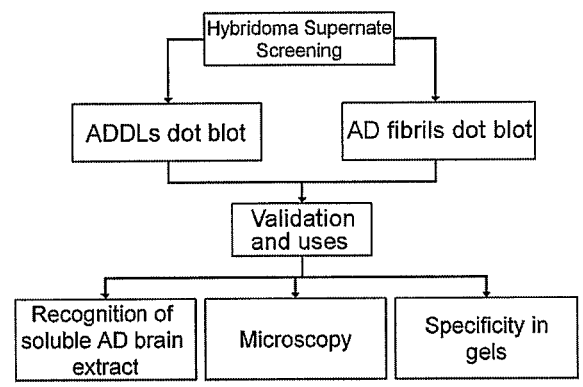
FIG. 1: Schematic representation of screening process used to develop oligomer-selective monoclonal antibodies against Aβ 1-42. As detailed herein, mice were inoculated with ADDLs (~194 μg/injection/mouse) every three weeks for six inoculations. Hybridomas produced from the fusion of these mouse spleens with SP2 cells were plated in 96-well plates and screened in two types of dot blots as shown. Promising hybridomas were subcloned and positives were then validated using various assays, e.g., Western blots, soluble extracts from AD brain (containing endogenous ADDLs) dot blots, and immunocyto/histochemistry. Selected antibodies were collected from culture medium and further purified using Protein G Sepharose.

General techniques for the generation, preparation, characterization, and use of antibodies are well known to persons skilled in the art (see e.g. Harlow, E. & Lane, D. (1988) *Antibodies: A Laboratory Manual*, Cold Spring Harbor Laboratory, Cold Spring Harbor: N.Y.; Harlow, E. & Lane, D. (1999) *Using Antibodies: A Laboratory Manual*, Cold, Spring Harbor Laboratory Press, Cold Spring Harbor: N.Y.; Sambrook, J. et al. (1989) *Molecular Cloning: A Laboratory Manual*, Cold Spring Harbor Laboratory Press, Cold Spring Harbor: N.Y.; and the like).

EXAMPLE 1

Anti-ADDL Antibodies

Development and Characterization

Materials and Methods

Monoclonal antibody development. Immunization and fusion were done at the Northwestern University Core Antibody Facility and at Immuno-Precise Antibodies, Ltd., Victoria, B.C., Canada. Growth, screening, and subcloning (when necessary) were performed in the laboratory of Dr. William Klein at Northwestern University.

At Northwestern, ADDLs in F12 medium, prepared from Aβ 1-42 as previously described [22;27], were mixed 1:1 with complete Freund's adjuvant (first and second vaccination) or incomplete Freund's adjuvant (all subsequent vaccinations) and injected subcutaneously (first two vaccinations) or intraperitoneally into 3 mice in a total volume of ~1 ml/mouse. Each injection consisted of ADDLs equivalent to 194±25 ug total protein. Mice were injected approximately every three weeks. After six injections, one mouse died and its spleen was frozen for future projects. The spleen from the mouse with the highest titer serum was then fused with SP2.0 myeloma cells and plated out into six 96-well plates. Supernatants from these plates were screened as stated below. The last mouse was injected a seventh time two months later and fused as before. The hybridoma cells were plated into twenty 96-well plates and grown at 37° C., 5% $CO_2$. Growth medium was DMEM/F12, supplemented with HAT (1x, Sigma), glutamine (2 mM), hybridoma enhancing supplement (10%, Sigma), OPI (oxaloacetate, purine, and insulin, 0.1%, Sigma), PMA (phorbol monoamine acetate, 0.6 ug/l, Sigma), fetal calf serum (0.15%), and Fetal Clone II serum (15%, HyClone). These plates were transferred to the Klein lab, where the supernates were screened as below. Selected hybridomas were expanded and frozen for later subcloning. Two hybridomas were subcloned without freezing.

The screening process eventually employed five assays: a dot immunoblot and Western immunoblot, described in [27], and native immunoblot, described below, using synthetic ADDLs, and a dot immunoblot and Western blot using endogenous fibrils obtained from human tissue, described below. These assays tested the binding of antibodies to ADDLs (dot immunoblot) and affinity to specific oligomer species (Western). Supernatants were initially tested by dot immunoblot using 5 pmole ADDLs (576 supernates in the first fusion and 1920 supernates in the second). Those clones that tested positive were further screened using Western blot at 10-20 pmole ADDLs/lane. The screen was repeated to identify low positives or false positives. Ten wells were expanded for the first mouse and forty-five for the second mouse, then frozen or subcloned.

Immuno-Precise Antibodies, Ltd., (Victoria, BC, Canada) was employed to produce clones using their proprietary Rapid-Prime method. The animals were immunized with ~0.25-0.35 ml ADDLs over a period of two weeks at an average of 0.505 mg/ml. Clone supernates (288/project) were then sent to the Klein laboratory for screening as above.

Preparation of synthetic and endogenous ADDLs and fibrils: Synthetic ADDLs were prepared in F12 as described in [22;27]. Synthetic fibrils were prepared according to [40]. Endogenous ADDLs were extracted from AD brain tissue as described [15] omitting the concentration step. Endogenous fibrils were obtained using the same method of preparation, except the pellet was then incubated for 1 hr with 2% SDS in F12 and centrifuged at 220,000×g for 1 hr. The pellet, which contained fibrils, was then suspended in F12 and sonicated for 30-60 sec to suspend material for determination of protein concentration.

Dot immunoblot and peptide competition: Initial screening by dot blot was performed according to [27] applying either ADDLs (5 pmole/dot) or fibrils (1 ug/dot) to the nitrocellulose. For competition dot blots, ADDLs were applied to dry nitrocellulose in duplicate at various pmolar concentrations in 0.5 ul volume using a template derived from the SurfBlot apparatus. Blots were then dried for 15 min, blocked for 1 hr, and inserted into the SurfBlot apparatus. Antibody plus or minus peptide was incubated in the wells for 1.5 hr, removed from the dot blot apparatus, the wells washed with blocking buffer, and the membrane removed from the apparatus. The nitrocellulose was then washed, treated with secondary antibody, and visualized as cited below.

Immunoblotting. Sodium dodecyl sulfate polyacrylamide gel electrophoresis (SDS-PAGE) was performed according to [27] except that 10-20% Tris-Tricine gels (BioRad) were used and the separation was performed at 120 V. The secondary antibody was routinely used at 1:40,000 dilution.

For initial screening, a preparative 10-20% gel was used with 2.7 µg ADDLs in the sample well, which is equivalent to ~16-20 pmol/lane. Electrophoresis and transfer were as above. Using the tracking dye as a guide, the blocked nitrocellulose was placed into the Surfblot apparatus and 200 ul of hybridoma supernate mixed with blocking buffer (5% nonfat dry milk in TBST—Tris-buffered saline with Tween 20—see [27]) were added to each of 20-21 wells. After incubation at room temperature for 1.5 hr, the supernates were removed and the wells washed with buffer. The membrane was then removed from the Surfblot and washed 3×15 min in TBST. The secondary antibody was then incubated with the membrane for 1 hr at RT. After washing (3×15 min), the oligomers were visualized with half strength SuperSignal (Pierce). The Western immunoblot using human fibrils was performed in the same manner using approximately 64 ug of prepared material for each gel.

Native polyacrylamide gel electrophoresis was performed according to [7] at 120 V.

Immunocytochemistry: Immunocytochemistry was performed as described in [27], except cultures were 21 DIV and AlexaFluor 488 (Molecular Probes) was used to visualize mouse IgG. In the blocking experiment, antibodies and ADDLs were preincubated for 1 hr at RT, using a molar ratio of 1:4 antibody:ADDL, before application to the hippocampal cell cultures.

Size Exclusion Chromatography: Size exclusion chromatography was performed as in [7]. Streptavidin-Dynabeads (50 µl, Dynal) were blocked in 1% BSA in PBS for 30 min at 4° C. Beads were incubated with biotinylated 20C2 (25 µg in 250 µl PBS) for 70 min at 4° C. and washed 3×10 min with 1 ml PBS. The beads, with or without antibody, were then incubated with ADDLs (40 µl, 25 µM) for 70 min at 4° C. and centrifuged at 15,000×g for 10 min. An aliquot (30 ul) of the supernatant was analyzed by SEC on a Superdex 75 PC 3.2/30 column equilibrated with PBS (0.06 ml min) and fractions (0.3 ml) collected. Absorbance was monitored at 215 nm.

Immunohistochemistry: Lightly fixed frozen sections (4% paraformaldehyde at 4° C. for 30 hrs, then cryoprotected in sucrose, 40 um) from AD and control hippocampus were incubated with antibody (1:1000 in PBS) overnight at 4° C. After removal of antibody, sections were washed 3 times with PBS and then incubated with the appropriate secondary antibody at 1:500 overnight at 4° C. Sections were rinsed 3× with PBS and incubated for 2 hrs at 4° C. with Vector ABC peroxidase standard kit. Binding was then visualized with DAB (0.05% or 1:500 in Tris buffer for 2 min). Sections were counterstained with hematoxylin, mounted with Permaslip, and imaged on a Nikon Eclipse E600 light microscope with a Spot Insight digital video camera (v. 3.2).

Results:

Oligomer-Specific Monoclonal Screening Strategy

To identify clones that recognize oligomers instead of monomer and/or fibrils, supernatants were screened initially by dot immunoblots using 5 pmol of synthetic ADDLs or 1 ug of endogenous AD fibrils (FIG. 1). Positives from this screen (~30%) were then tested by Western immunoblots to further define binding species. Of the clones tested by Western blots, ~2% were found to bind oligomers and not monomer at low ADDL concentrations. Most of these clones also bound fibrils and one (20C2) was selected for characterization in depth. One clone (1H9) was found that bound the higher multiple oligomers (12-24mer) better than the trimer/tetramer species. One clone (3A5) was found that bound ADDLs only under native conditions. Two clones were found that bound fibrils and not oligomers (3A7, 3A9). Approximately 50 clones were selected for future expansion, purification, and testing.

Monoclonals Specifically Distinguish AD from Control Brain

Figure 2:
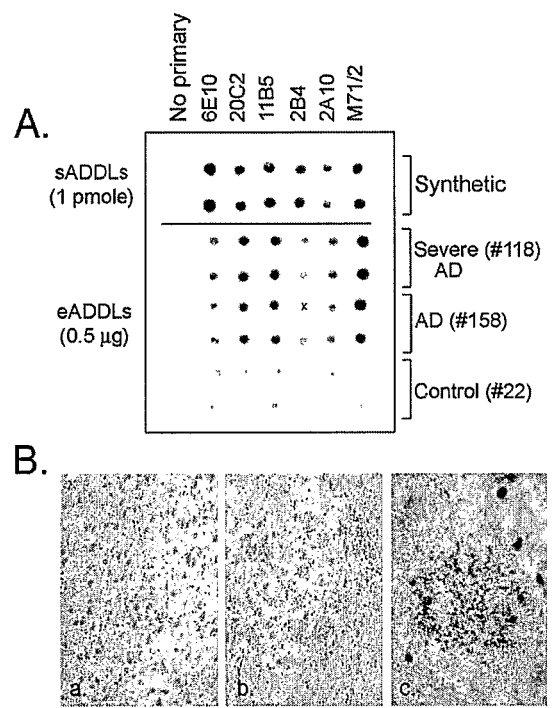
FIG. 2: Selected antibodies discriminate between AD and control brain tissue. A. Synthetic ADDLs (1 pmol) and human brain extracts in F12 (from human AD and control brain; 0.5 μg, see Methods) were spotted onto nitrocellulose in duplicate. After peroxidase treatment (3% $H_2O_2$, 20 min.) and blocking, each vertical lane was then probed with the indicated monoclonals or rabbit polyclonal (M71/2) for 1 hr at room temperature. After washing, the nitrocellulose was incubated with the appropriate HRP-conjugated secondary antibody; bound secondary was then visualized with chemiluminescence. Note that 20C2, 11B5, and M71/2 bind strongly to AD brain samples but not to control brain samples. B. a-c: Hippocampal sections (40 μm) prepared from control (a) and Alzheimer's (b,c) brain were incubated with the monoclonal 20C2 overnight at 4° C. Bound antibody was then visualized with anti-mouse HRP secondary and DAB. The samples were then counterstained with hematoxylin. Oligomers are found extensively in AD brain (b) but not control brain (a)(200×). Higher magnification (c) shows that staining surrounds the cell body in a perineuronal pattern (600×).

An essential test was to determine if the antibodies could distinguish between soluble extracts of human AD brain (containing endogenous ADDLs) and extracts of control brain. Synthetic ADDLs (1 pmole) and three human brain extracts (0.5 µg, staged for Braak and CERAD grades) were assayed by dot immunoblot. A representative result is shown in FIG. 2A. 6E10 (a commercial antibody with epitope within Aβ 3-8), 2B4, and 2A10 showed weak binding to AD brain extract but still discriminated between AD and control brain. However, two monoclonals, 20C2 and 11B5, along with polyclonal M71/2, distinguished between AD and control brain with a high degree of specificity.

20C2 Immunoreactivity in AD Brain

20C2 next was tested for its ability to detect antigen in human brain sections. Fixed AD and control brain were exposed to antibody and then counterstained with hematoxylin. Immunoreactivity was prominent in the hippocampus, entorhinal cortex, and middle frontal gyrus of AD brain (FIG. 2B, middle). The labeling was varied, consisting of plaque-like regions and vascular elements. The control brain showed no staining with 20C2 (FIG. 2B, left). Additionally, an intriguing pattern of diffuse labeling was found surrounding individual neurons and cell clusters (perineuronal staining, FIG. 2B, right), as seen with polyclonals previously [25]. The perineuronal labeling resembles binding of oligomers to dendritic sites seen in culture[25].

Specificity of 20C2: Western and Dot Immunoblots

The ability of 20C2 to bind Aβ 1-40 was then tested, ADDLs, and ADDL fractions separated by SEC using a Superdex 75 column. As previously reported, the SEC provided two major fractions, Peak 1, which elutes shortly after the void volume, and Peak 2, which elutes near a 13 kDa marker [7;25]. For comparison, the binding of 6E10 and M71/2 was also tested. SDS-PAGE was followed by silver stain (FIG. 3A) or immunoblotting (FIG. 3B). Only 6E10 recognized Aβ1-40, which migrated exclusively as a monomer. 6E10 also gave prominent staining of monomeric Aβ 1-42 in all three fractions. The low molecular weight Peak 2 was primarily monomer. 20C2 and M71/2, in contrast to 6E 10, showed only faint staining of monomer in Peak 2 and no staining of monomers in Peak 1 or unfractionated ADDLs. All three antibodies showed reaction with trimer, tetramer, and 12-24mer found in ADDL preparations and Peak 1. Western blots thus indicate that 20C2 has strong preferential binding for oligomers over monomers.

Validation of Selectivity for Oligomers

Three additional tests of specificity were carried out. First, the time-dependent formation of oligomers from 10 nM monomeric Aβ1-42 (FIGS. 3C and D) was measured by dot immunoblot. At the outset, when monomers would predominate, staining was light. Over the next 10 minutes oligomerization was relatively rapid, and immunoreactivity increased 400%. Aβ1-40 monomers were detected poorly (FIG. 3C). In harmony with Western blots, these assays of undenatured molecules bound to nitrocellulose indicate 20C2 is selective for oligomers.

Next, immunoprecipitation was used to determine if 20C2 selectively recognized ADDLs over monomers in solution. Magnetic Dynabeads with or without 20C2 were incubated with ADDLs, beads plus bound material removed, and the supernatants fractionated using a Superdex 75 column (not shown). Higher molecular weight species found in Peak 1 were selectively removed compared to Peak 2 (73% vs 33%). Peak 2 comprises low molecular weight oligomers but primarily monomers. Results are consistent with solution selectivity of 20C2 for oligomers over monomers.

Figure 3:
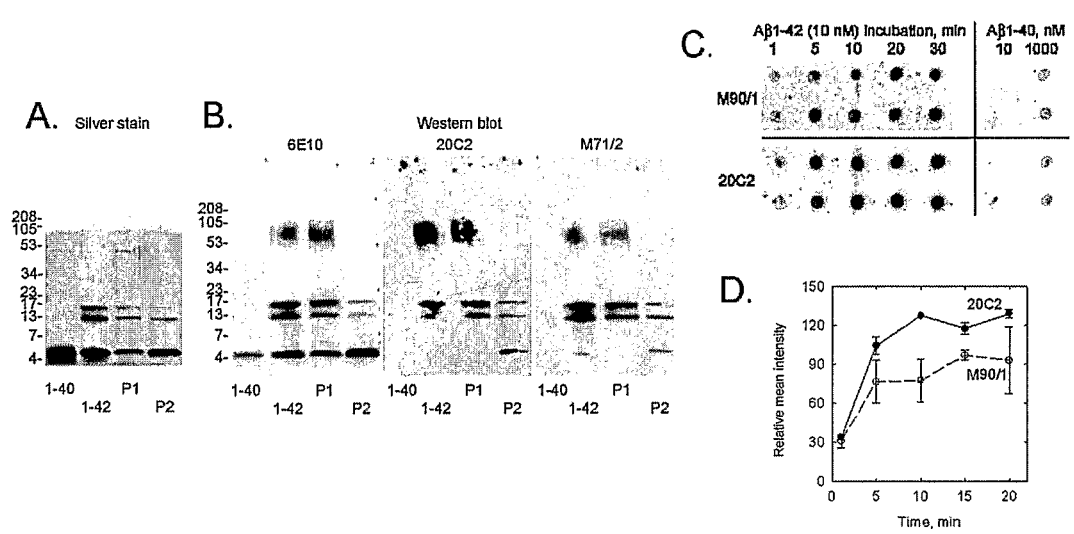
FIG. 3: 20C2 shows minimal monomer detection of Aβ peptides. Aβ 1-40, ADDLs, and ADDLs resolved into two peaks by SEC [7] were separated by SDS-PAGE using 10-20% Tris-Tricine gels. One gel was silver stained (A) while other samples were transferred to nitrocellulose and then probed with 6E10, 20C2, and M71/2 (B). On silver stain, Aβ 1-40 showed only a heavy monomer band. ADDLs and the separated ADDL peaks all have monomer, trimer and tetramer bands of various intensities. In the Western analysis, 6E10 identified monomer bands in all four samples, with ADDLs and Peak 1 showing heavy trimer, tetramer, and 12-24mer bands, while Peak 2 showed primarily monomer with light trimer and tetramer. Both 20C2 and M71/2, on the other hand, showed minimal or no monomer staining with ADDLs and Peak 1, but heavy trimer, tetramer, and 12-24mer similar to 6E10. Peak 2 showed light monomer, trimer, and tetramer staining with 20C2 and M71/2, but no 12-24mer. Aβ 1-40 was not recognized by 20C2 or M71/2. In C and D, the aggregation of monomerized Aβ 1-42 peptide on ice was monitored by dot blot, comparing 20C2 and the rabbit polyclonal M90/1. Equal aliquots (20 fmol) of the solution were spotted at the times indicated and then probed with antibody. Both antibodies detected time-dependent ADDL formation from Aβ 1-42. Both antibodies also showed minimal signal with monomeric Aβ 1-40, even at 100-fold greater peptide concentration. In D, the relative intensity of the dot blots is shown as a function of time. These data are additional evidence that the monoclonal 20C2 is oligomer-specific.
Figure 4:
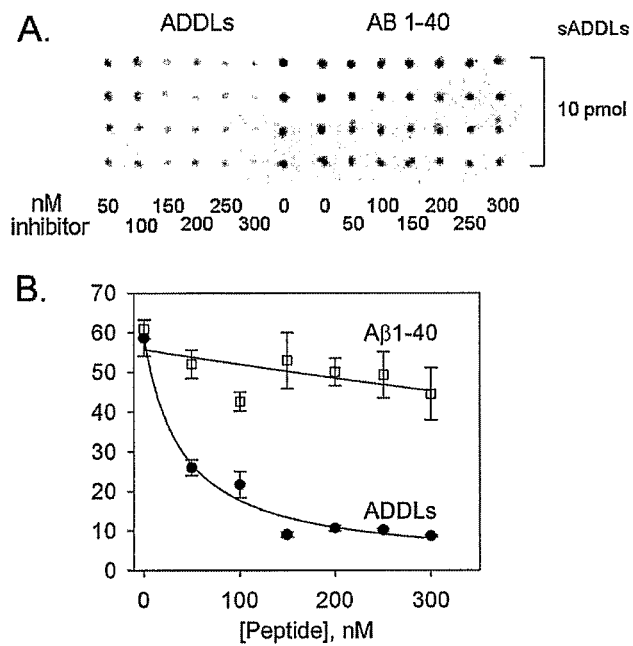
FIG. 4: Soluble ADDLs, but not monomeric Aβ 1-40, block 20C2 binding to low concentration immobilized ADDLs. In (A), ADDLs were applied to nitrocellulose at a concentration of 10 pmol/0.5 μl. After blocking, each lane was incubated for 1.5 hr with 20C2 that had been pre-incubated with either ADDLs or Aβ 1-40 at various concentrations as indicated. Binding of antibody was then determined by incubation with anti-mouse-HRP and chemiluminescence. The Kodak Image Station 440 was used to quantify blot intensity. These data were then plotted as a function of peptide concentration using SigmaPlot (B). ADDLs in solution effectively block 20C2 binding to immobilized ADDLs (half maximal blocking ~32 nM), whereas monomeric Aβ 1-40 shows only non-specific blocking.

Third, the affinity of 20C2 for ADDLs or Aβ1-40 in solution was compared using a competition assay. 20C2 was preincubated with increasing amounts of ADDLs or fresh Aβ1-40 and then tested for ability to bind to ADDLs immobilized on nitrocellulose (FIG. 4A). ADDLs in solution effectively blocked binding to immobilized ADDLs, with half maximal inhibition at 30 nM (FIG. 4B). Monomeric Aβ1-40 was ineffective at blocking binding, showing a linear decrease indicative of a non-specific association. Non-specific association is consistent with the low level of reactivity seen earlier (FIG. 3C).

Conformational Nature of 20C2 Epitope

To investigate the epitope for 20C2, competition dot immunoblots first were carried out using four short peptides that encompassed the entire length of Aβ1-42 (1-12, 12-28, 25-35, 35-42). None of the peptides had any effect on binding of 20C2 to ADDLs (FIG. 5A), while ADDL controls completely blocked binding. Next, the longer peptides Aβ1-28 and Aβ17-42 were assayed. Binding of 20C2 to ADDLs was completely inhibited by Aβ1-28 (FIG. 5B). Half maximal inhibition was at 10 nM (FIG. 5C), slightly lower than with ADDLs. Since ADDLs are in a mixed solution that includes monomers, this difference is not surprising. Aβ17-42 had no impact nor did any combination of peptides. Preincubation of 20C2 with Aβ1-28 also blocks binding in Western blots (FIG. 5D). The conformational epitope of Aβ1-28 could derive from tertiary or quaternary structure. It previously has been suggested [28] that Aβ1-28 forms a dimer and when analyzed by SDS-PAGE (FIG. 5D), our preparation migrates as a single band consistent with this suggestion. This dimer however was not recognized by 20C2 in Western blots.

Immunoneutralization of ADDL Binding to Cells

Figure 6:
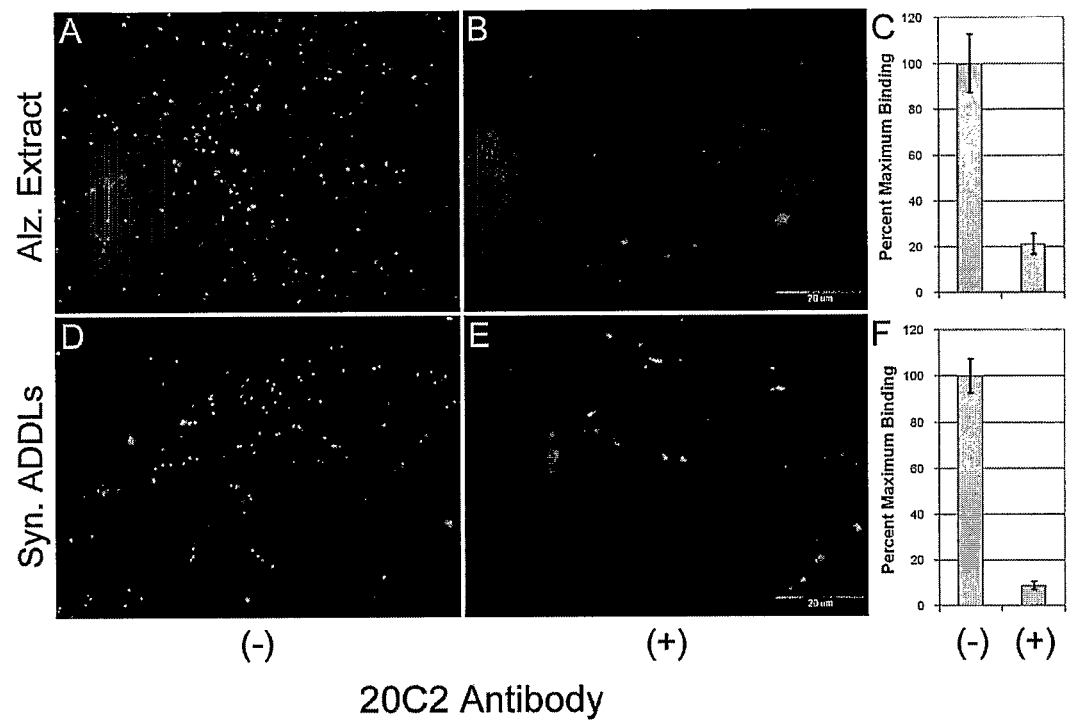
FIG. 6: 20C2 neutralizes binding of endogenous and synthetic ADDLs to cultured cells. Three-week-old cultured hippocampal cells were incubated with either soluble extract from AD brain containing endogenous ADDLs (A) or synthetic ADDLs (B) for 60 min. After removing unbound ADDLs by washing with warm culture medium, bound ADDLs were identified with 20C2 and anti-mouse-AlexaFluor 488 (See Methods). To test for immunoneutralization, ADDLs were preincubated with 20C2 for 1 hr at 37° C. prior to incubation with cultured hippocampal cells as above. After washing, anti-mouse AlexaFluor 488 was used to identify bound antibody. 20C2 blocked binding of both soluble extract from AD brain containing endogenous ADDLs (C) and synthetic ADDLs (D) to hippocampal cultures. Control plates in which fresh 20C2 was added to cells before AlexaFluor 488 also showed no ADDL binding. Quantification of binding hot spots with and without 20C2 preincubation is shown in (E). p=0.005.
Figure 7:
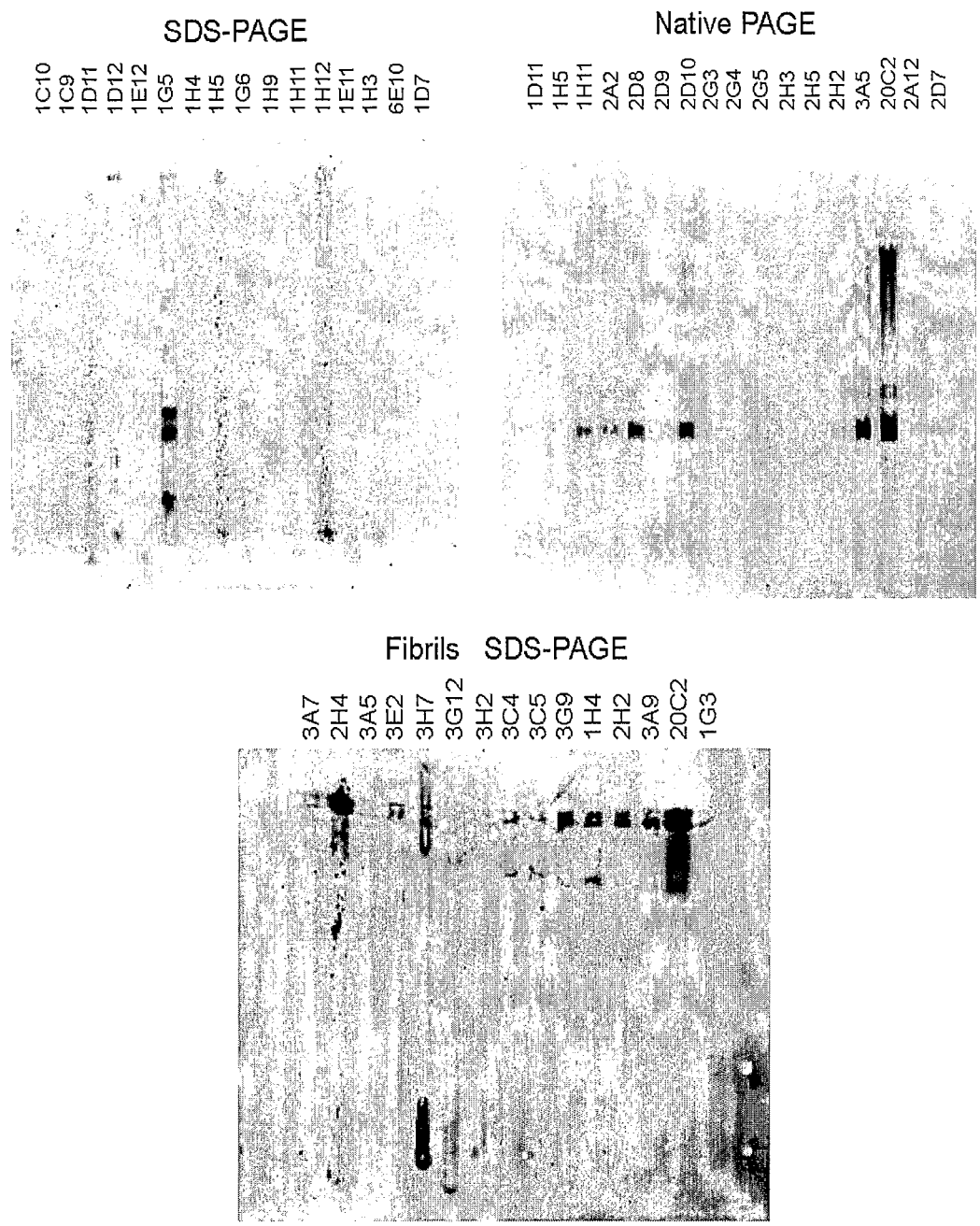
FIG. 7: Screening methods highlight differences among ADDL-generated monoclonal antibodies. Mice were inoculated with ADDLs using two different protocols. The standard 5-month inoculation period and fusing methods were employed by the Northwestern University Core Antibody Facility, whereas Immuno-Precise, Inc. (British Columbia, Canada) used a 2-week inoculation period with a picked selection process. Hybridoma supernatants were then sent to us for screening. Our first screen was an ultrasentitive dot blot assay (Lambert, M. P. et al. (1998) Proc. Natl. Acad. Sci. USA, vol. 95, pp. 6448-6453) utilizing first ADDLs and then fibrils from AD brain for the recognition molecules. Positive wells were then screened in a Western protocol, using ADDLs under both denatured (Left, top) and native (Right, top) conditions. Lastly, fibrils from AD brain were used in a Western protocol (Bottom) to determine final selections.
Figure 9:
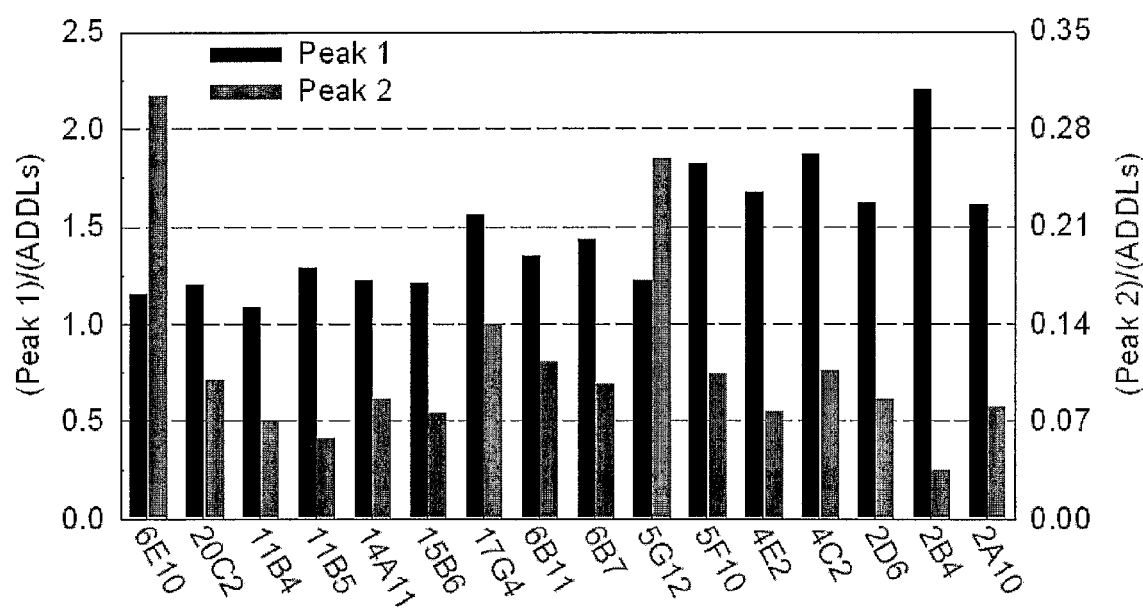
FIG. 9: ADDL-generated monoclonal antibody clones show differences in detection of ADDLs separated by size exclusion chromatography (SEC). A sandwich ELISA was developed using polyclonal antibody M90 to ADDLs as the capture antibody. SEC peak 1 and peak 2 fractions refer to the two major peaks of ADDLs that were fractionated on a Sephadex 75 column (in order to distinguish between potentially bioactive and inactive oligomers, "synthetic" ADDLs were subjected to gel filtration chromatography, which produced two major peaks; non-denaturing gel electrophoresis confirmed the separation into large (>50 kDa) and small (<30 kDa) aggregates that are stable at 37° C). These peaks were used separately as the detection substance for clone supernates. Binding was visualized with a Vectastain kit. Data were quantified using SigmaPlot software. Differences between recognition of the two peaks are seen with all antibodies. For example, compare the ratio of peak 1 to peak 2 for antibodies 2B4 and 20C2. Only one antibody reflects the control antibody (6E 10) preference for peak 2.
Figure 10:
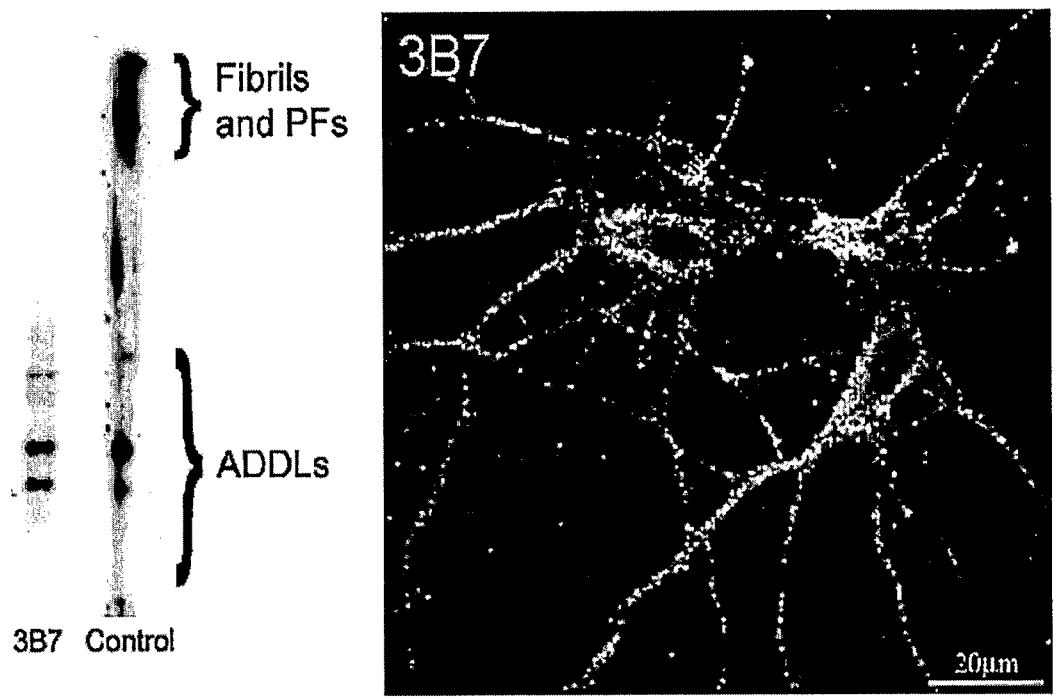
FIG. 10: ADDLs are oligomeric when bound to cultured cells. (Left) Western immunoblot showing 3B7 monoclonal and M94 polyclonal binding to a synthetic solution containing ADDLs and fibrils. Note lack of binding to fibrils, higher molecular weight oligomers, and monomer by 3B7. (Right) Image of ADDLs bound to 3-week old cultured hippocampal cells detected by 3B7 and visualized by AlexaFluor® 488 anti-mouse IgG. Since 3B7 does not recognize fibrils or monomer, the hot spot binding of ADDLs is oligomeric.
Figure 11:
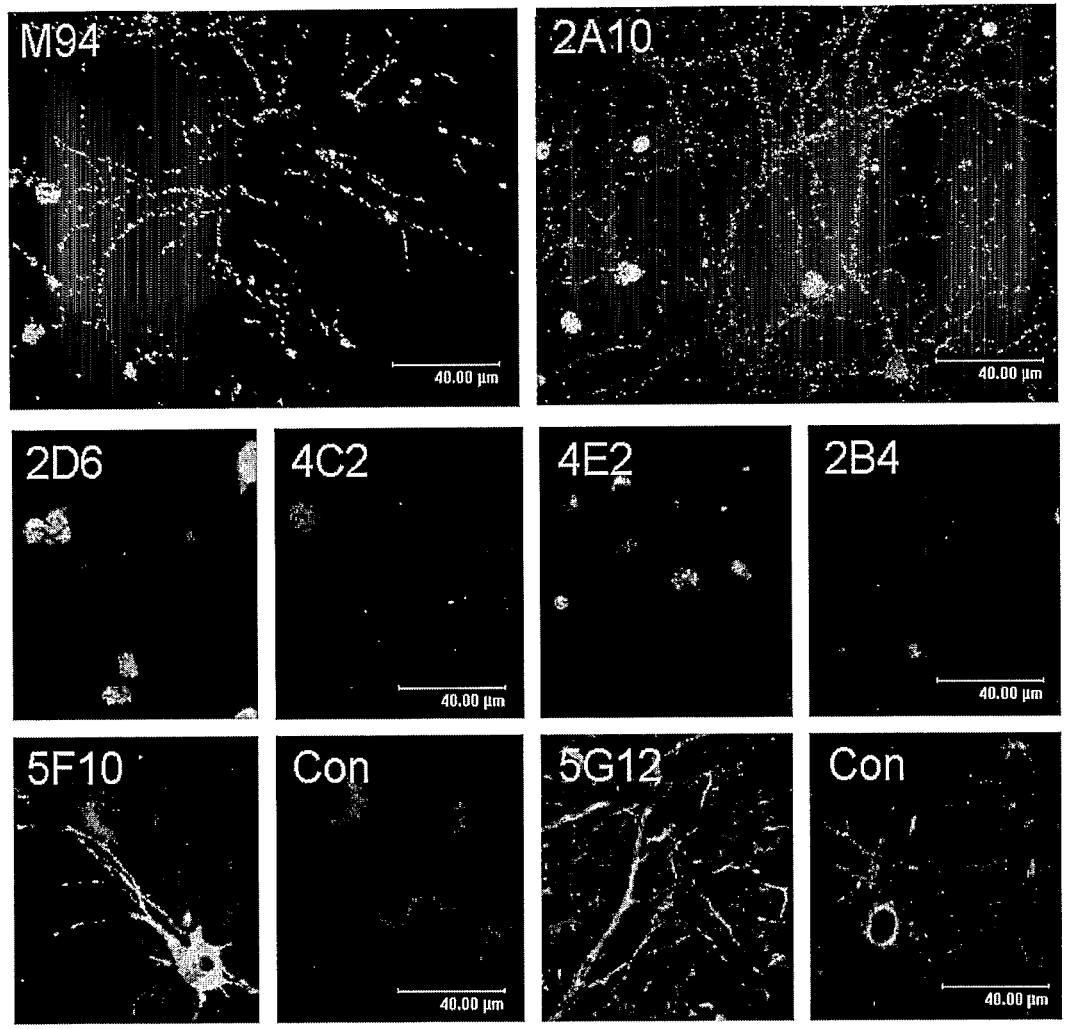
FIG. 11: ADDL-generated monoclonal antibodies show differential binding to ADDL-treated cultured cells. Cultured hippocampal cells obtained from E18 rats were grown for three weeks as stated in Example 2. Cells were then exposed for 1 hr to ADDLs (500 nM), washed, and fixed. ADDLs were identified with the indicated antibodies and visualized with AlexaFluor® 488-anti-mouse IgG. Antibodies appear to recognize different epitopes on ADDLs bound to cells, ranging from hot spots on processes (M94, 2A10) to cell body specific attachment (4E2) and other states in between (2D6, 4C2, 2B4, 5F10, 5G12).

ADDLs, whether formed in vitro or obtained from AD brain, attach to synapses in hippocampal cultures [25]. In the final experiment, 20C2 was tested for its ability to inhibit this synaptic binding. ADDLs, pretreated with or without 20C2, were incubated with cultures for 60 min and ADDL binding detected by immunofluorescence microscopy (FIG. 6). Without 20C2, ADDLs bound with a punctate synaptic pattern as previously observed [25;27]. Vehicle and no-secondary antibody controls showed no staining. Binding of AD brain-derived (5C) and synthetic (5D) ADDLs both were blocked by preincubation with 20C2. Inhibition of binding by 20C2 under these conditions exceeded 90% (5E).

Discussion

ADDLs were used to generate monoclonal antibodies that targeted pathological Aβ assemblies. Three types of antibodies of interest were generated: those capable of binding oligomers and fibrils; those capable of binding fibrils but not oligomers; and those capable of binding oligomers but not fibrils. The first class was most common, and one particular clone of this class was expanded and characterized in depth (20C2). This antibody discriminated AD from control brains in extracts and in tissue sections. Discrimination derived from a 3D epitope common to ADDLs and assemblies of Aβ1-28 that was absent from Aβ1-40 and other linear sequences. Binding of ADDLs by 20C2 prevented their binding to synapses in hippocampal cultures. 20C2 thus is a prototype for therapeutic monoclonal antibodies that selectively immunoneutralize pathological Aβ assemblies.

Immunization with various forms of Aβ fragments and assemblies has generated antibodies with a variety of useful properties. Short N-terminal peptides, e.g., generated the 6E10 [21] used in the current study, which binds to virtually all forms of Aβ. C-terminal antigens produced monoclonals that distinguish Aβ1-40 from Aβ1-42 making them useful for selective ELISAs [19;34]. Kayed et al [20] recently used Aβ1-40 coupled to gold colloids to generate antibodies that bind oligomers but not monomers or fibrils in vitro and that in brain sections react with diffuse, early-stage plaques but not thioflavin-positive dense-core plaques. Polyclonal antibodies generated by vaccination with ADDL preparations [27] have been used to distinguish AD brain tissue from control in both slices and dot immunoblots, to characterize the nature of oligomers in AD brain, to identify ADDLs bound to synapses on cultured cells, and to identify lead compounds for anti-ADDL drug discovery [25;27;43].

The 20C2 monoclonal resembles ADDL-generated polyclonal antibodies in recognizing oligomers and fibrils but not monomer in Western and dot immunoblot paradigms. In AD brain sections, light perineuronal immunoreactivity was evident. This immunoreactivity has been attributed hypothetically to oligomer attachment to synapses, thought to occur early in AD or even preclinically. The species recognized by 20C2 in Western blots prominently included higher order oligomers (12-24mers) even though no material was detected by silver stain. Aβ1-40 monomer was not recognized in immunoblots by 20C2, nor was Aβ1-42 monomer recognized when SDS was present in transfer buffer. Without SDS, however, 20C2 showed immunoreactivity at the monomer position. Transfer of monomer was unaffected by SDS, verified in streptavidin-HRP assays for biotinylated Aβ1-42 (data not shown). Without being bound by any one explanation or mechanism, it is hypothesized that without SDS monomers combine during transfer and produce oligomers, consistent with the rapid oligomerization seen even at very low Aβ concentrations (FIG. 3). Competition experiments verified that 20C2 had minimal affinity for monomers in solution, circumventing the ambiguities associated with SDS-PAGE analysis.

Figure 5:
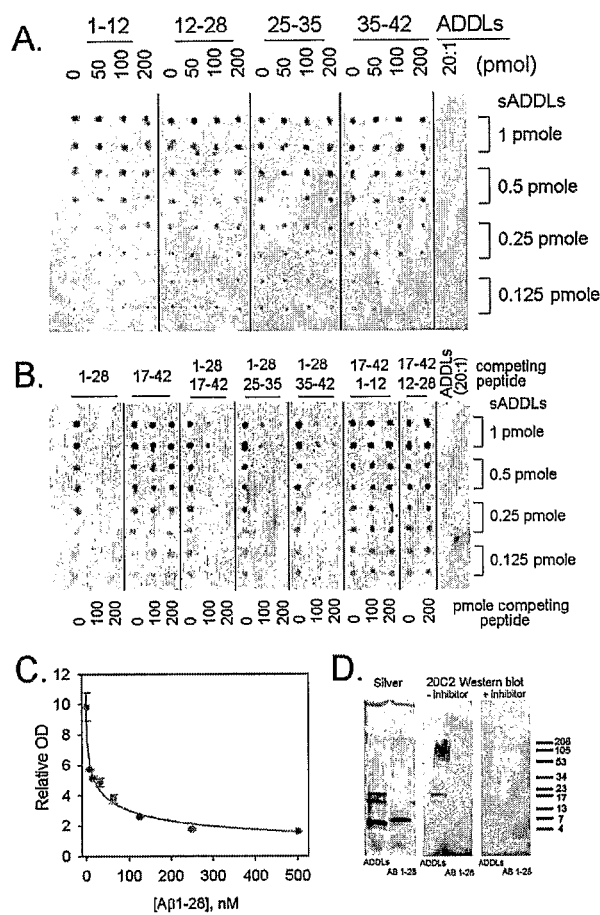
FIG. 5: The soluble peptide Aβ 1-28 blocks 20C2 binding to ADDLs. Studies to investigate the epitope of 20C2 used incubation with four short linear peptides of 8-17 amino acids covering the entire length of Aβ-1-42 to block binding of the antibody to immobilized ADDLs. None of the tested peptides blocked binding, even at 100-fold excess over antibody (A). Two longer peptides were then tested in a similar assay, with the result that Aβ 1-28 showed excellent blocking ability (B), either alone or in combination with other peptides. The blocking effectiveness of Aβ 1-28 was similar to ADDLs, with an estimated half-maximal blocking near 11 nM (C). Aβ 1-28 also blocked 20C2 binding to denatured ADDLs in an SDS-PAGE immunoblot. (D).

Competition experiments (FIG. 5) further showed that 20C2 binding to ADDLs depended on conformational determinants, consistent with previous suggestions of Aβ1-42 antigenicity [8]. Preincubation of 20C2 with solutions containing ADDLs or Aβ1-28 blocked subsequent binding to ADDLs in dot immunoblots. Other peptides, including Aβ1-40, were without effect. Analysis of Aβ1-28 by electrospray mass spectrometry indicates it forms dimers and possibly other higher order oligomers in the gas phase [28]. Two dimer structures were hypothesized to fit the data, with core overlaps of either Aβ17-23 or Aβ17-28. It is therefore suggested that the 20C2 epitope is three-dimensional, in which aggregation of Aβ1-28 to form a dimer is necessary to align correct amino acids in the binding pocket, perhaps some from each single peptide. Denatured Aβ1-28 migrates at a position consistent with dimer, as seen by silver stain (FIG. 5). Alternatively, the single peptide itself could fold to align amino acids in the proper sequence whereas the shorter peptides, as well as full-length Aβ1-40, could not.

Antibodies with N-terminal epitopes appear to be more effective than C-terminal or central epitopes at plaque clearance in tg mice [3] and at inhibition of fibrillogenesis and cytotoxicity [29]. A substituted single chain antibody that relies on the Aβ3-6 sequence (EFRH) suppressed in vitro formation of Aβ aggregates and caused a loss of brain amyloid burden in tg mice [12;39]. Another N-terminal antibody, BAM-10, caused reversal of memory impairment in tg mice with no decrease in amyloid plaques [24]. The antibody was hypothesized to act by neutralizing soluble Aβ assemblies in the brain that cause cognitive impairment. A second antibody, M266, generated against the central domain Aβ 13-28, also caused reversal of memory deficits [10]. The reversal occurred after only 24 hours with no change in brain Aβ plaques. Since this antibody alters clearance of CNS and plasma Aβ [38], the authors suggest that the antibody is acting as a sink for Aβ, leading to CNS clearance [9].

Success of active and passive vaccinations in mouse AD models led to clinical trials for an active vaccine in AD patients [36;37]. Phase 2 trials were stopped due to the appearance of meningoencephalitis in 6% of the patients [17] [33], but early clinical data from immunotherapy have been encouraging, and efforts are underway to develop alternative Aβ immunotherapies [13]. Active vaccines are being developed using immunoconjugates composed of a fragment of Aβ, usually from the N-terminal or central region, linked to a carrier protein [37]. These antigens contain no epitopes from Aβ 1-42 that will initiate a T-cell response, which may eliminate autoimmune reactions. Passive vaccines also are being developed, which present advantages in avoiding poor immune responses in older patients as well as eliminating the T-cell response to Aβ. It has been previously suggested that development of therapeutic antibodies that target ADDLs may optimize the efficacy of this approach [23]. The present invention establishes that relatively potent monoclonal antibodies can be generated using synthetic ADDLs as immunogens, and that the resultant antibodies are selective for pathological assemblies of Aβ. The antibodies, moreover, immunoneutralize ADDLs obtained from AD brain, blocking their attachment to synapses in cell culture assays. The antibodies thus have promise for use in future behavioral studies of ADDL neutralization in tg-mice AD models and provide a step toward antibodies of clinical value ADDL-selective monoclonal antibodies are also useful for AD diagnostics. In recent studies, ADDL-selective antibodies were combined with developments in nanotechnology to develop assays capable of detecting ADDLs in human CSF (Georganopoulou, D. G. et al. (2005) Nanoparticle-based detection in cerebral spinal fluid of a soluble pathogenic biomarker for Alzheimer's disease. Proc. Natl. Acad. Sci. USA 102(7):2273-76; Haes, A. J. et al. (2005) Detection of a biomarker for Alzheimer's disease from synthetic and clinical samples using a nanoscale optical biosensor. J. Am. Chem. Soc. 127(7):2264-71). The new assays are orders of magnitude more sensitive than the best available ELISAs, capable of detecting low atomolar ADDL concentrations. Results showing a ten-fold difference in CSF ADDL levels between AD and control subjects (Georganopoulou, D. G. et al. (2005) Nanoparticle-based detection in cerebral spinal fluid of a soluble pathogenic biomarker for Alzheimer's disease. Proc. Natl. Acad. Sci. USA 102(7):2273-76) suggest that nanotechnology-based assays in combination with ADDL-selective monoclonal antibodies could provide the first chemical diagnostics for AD.

References

[1] Agadjanyan M G, Ghochikyan A, Petrushina I, Vasilevko V, Movsesyan N, Mkrtichyan M, Saing T, Cribbs D H. Prototype Alzheimer's disease vaccine using the immunodominant B cell epitope from beta-amyloid and promiscuous T cell epitope pan HLA DR-binding peptide. J Immunol 2005 February; 174(3):1580-6.

[2] Bacskai B J, Kajdasz S T, McLellan M E, Games D, Seubert P, Schenk D, Hyman B T. Non-Fc-mediated mechanisms are involved in clearance of amyloid-beta in vivo by immunotherapy. J Neurosci 2002 September; 22(18):7873-8.

[3] Bard F, Barbour R, Cannon C, Carretto R, Fox M, Games D, Guido T, Hoenow K, Hu K, Johnson-Wood K, Khan K, Kholodenko D, Lee C, Lee M, Motter R, Nguyen M, Reed A, Schenk D, Tang P, Vasquez N, Seubert P, Yednock T. Epitope and isotype specificities of antibodies to beta-amyloid peptide for protection against Alzheimer's disease-like neuropathology. Proc Natl Acad Sci USA February 2000; 100(4):2023-8.

[4] Bard F, Cannon C, Barbour R, Burke R L, Games D, Grajeda H, Guido T, Hu K, Huang J, Johnson-Wood K, Khan K, Kholodenko D, Lee M, Lieberburg I, Motter R, Nguyen M, Soriano F, Vasquez N, Weiss K, Welch B, Seubert P, Schenk D, Yednock T. Peripherally administered antibodies against amyloid beta-peptide enter the central nervous system and reduce pathology in a mouse model of Alzheimer disease. Nat Med August 2000; 6(8):916-9.

[5] Birmingham K, Frantz S. Set back to Alzheimer vaccine studies. Nat Med March 2002; 8(3):199-200.

[6] Chang L, Bakhos L, Wang Z, Venton D L, Klein W L. Femtomole immunodetection of synthetic and endogenous amyloid-beta oligomers and its application to Alzheimer's disease drug candidate screening. J Mol Neurosci 2003; 20(3):305-13.

[7] Chromy B A, Nowak R J, Lambert M P, Viola K L, Chang L, Velasco P T, Jones B W, Fernandez S J, Lacor P N, Horowitz P, Finch C E, Krafft G A, Klein W L. Self-assembly of A beta(1-42) into globular neurotoxins. Biochemistry November 2003; 42(44): 12749-60.

[8] Cribbs D H, Ghochikyan A, Vasilevko V, Tran M, Petrushina I, Sadzikava N, Babikyan D, Kesslak P, Kieber-Emmons T, Cotman C W, Agadjanyan M G. Adjuvant-dependent modulation of Th1 and Th2 responses to immunization with beta-amyloid. Int Immunol April 2003; 15(4):505-14.

[9] DeMattos R B, Bales K R, Cummins D J, Dodart J C, Paul S M, Holtzman D M. Peripheral anti-A beta antibody alters CNS and plasma A beta clearance and decreases brain A beta burden in a mouse model of Alzheimer's disease. Proceedings of the National Academy of Sciences of the United States of America July 2001; 98(15):8850-5.

[10] Dodart J C, Bales K R, Gannon K S, Greene S J, DeMattos R B, Mathis C, Delong C A, Wu S, Wu X, Holtzman D M, Paul S M. Immunization reverses memory deficits without reducing brain A beta burden in Alzheimer's disease model. Nature Neuroscience 2002 May; 5(5):452-7.

[11] Ferrer I, Boada R M, Sanchez Guerra M L, Rey M J, Costa-Jussa F. Neuropathology and pathogenesis of encephalitis following amyloid-beta immunization in Alzheimer's disease. Brain Pathol 2004 January; 14(1): 1-20.

[12] Frenkel D, Katz O, Solomon B. Immunization against Alzheimer's beta-amyloid plaques via EFRH phage administration. Proc Natl Acad Sci USA 2000 October; 97(21):11455-9.

[13] Gelinas D S, DaSilva K, Fenili D, George-Hyslop P, McLaurin J. Immunotherapy for Alzheimer's disease. Proc Natl Acad Sci USA 2004 October; 101 Suppl 2:14657-62.

[14] Georganopoulou D G, Chang L, Nam J M, Thaxton C S, Mufson E J, Klein W L, Mirkin C A. Nanoparticle-based detection in cerebral spinal fluid of a soluble pathogenic biomarker for Alzheimer's disease. Proc Natl Acad Sci USA 2005 February.

[15] Gong Y, Chang L, Viola K L, Lacor P N, Lambert M P, Finch C E, Krafft G A, Klein W L. Alzheimer's disease-affected brain: presence of oligomeric A beta ligands (ADDLs) suggests a molecular basis for reversible memory loss. Proc Natl Acad Sci USA 2003 September; 100(18): 10417-22.

[16] Haes A J, Chang L, Klein W L, Van Duyne R P. Detection of a biomarker for Alzheimer's disease from synthetic and clinical samples using a nanoscale optical biosensor. J Am Chem Soc 2005 February; 127(7):2264-71.

[17] Hock C, Konietzko U, Streffer J R, Tracy J, Signorell A, Muller-Tillmanns B, Lemke U, Henke K, Moritz E, Garcia E, Wollmer M A, Umbricht D, de Quervain D J, Hofmann M, Maddalena A, Papassotiropoulos A, Nitsch R M. Antibodies against beta-amyloid slow cognitive decline in Alzheimer's disease. Neuron 2003 May; 38(4):547-54.

[18] Janus C, Pearson J, McLaurin J, Mathews P M, Jiang Y, Schmidt S D, Chishti M A, Horne P, Heslin D, French J, Mount H T, Nixon R A, Mercken M, Bergeron C, Fraser P E, George-Hyslop P, Westaway D. A beta peptide immunization reduces behavioural impairment and plaques in a model of Alzheimer's disease. Nature 2000 December; 408(6815):979-82.

[19] Jensen M, Hartmann T, Engvall B, Wang R, Uljon S N, Sennvik K, Naslund J, Muehlhauser F, Nordstedt C, Beyreuther K, Lannfelt L. Quantification of Alzheimer amyloid beta peptides ending at residues 40 and 42 by novel ELISA systems. Mol Med 2000 April; 6(4):291-302.

[20] Kayed R, Head E, Thompson J L, McIntire T M, Milton S C, Cotman C W, Glabe C G. Common structure of soluble amyloid oligomers implies common mechanism of pathogenesis. Science 2003 April; 300(5618):486-9.

[21] Kim K S, Wen G, Bancher C, Chen J C, Sapienza V J, Hong H, and Wisniewski H M. Quantitation of amyloid b-protein with twomonoclonal antibodies. Neurosci Res Commun 1990; 7:113-22.

[22] Klein W L. Abeta toxicity in Alzheimer's disease: globular oligomers (ADDLs) as new vaccine and drug targets. Neurochem Int 2002 November; 41(5):345-52.

[23] Klein W L, Krafft G A, Finch C E. Targeting small Aβ oligomers—In the solution to an Alzheimer's disease conundrum? Trends Neurosci 2000; 24:219-24.

[24] Kotilinek L A, Bacskai B, Westerman M, Kawarabayashi T, Younkin L, Hyman B T, Younkin S, Ashe K H. Reversible memory loss in a mouse transgenic model of Alzheimer's disease. J Neurosci 2002 August; 22(15):6331-5.

[25] Lacor P N, Buniel M C, Chang L, Fernandez S J, Gong Y, Viola K L, Lambert M P, Velasco P T, Bigio E H, Finch C E, Krafft G A, Klein W L. Synaptic targeting by Alzheimer's-related amyloid beta oligomers. J Neurosci 2004 November; 24(45):10191-200.

[26] Lambert M P, Barlow A K, Chromy B A, Edwards C, Freed R, Liosatos M, Morgan T E, Rozovsky I, Trommer B, Viola K L, Wals P, Zhang C, Finch C E, Krafft G A, Klein W L. Diffusible, nonfibrillar ligands derived from Abeta1-42 are potent central nervous system neurotoxins. Proc Natl Acad Sci USA 1998 May; 95(11):6448-53.

[27] Lambert M P, Viola K L, Chromy B A, Chang L, Morgan T E, Yu J, Venton D L, Krafft G A, Finch C E, Klein W L. Vaccination with soluble Abeta oligomers generates toxicity-neutralizing antibodies. J Neurochem 2001 November; 79(3):595-605.

[28] Li A, Fenselau C. Contact regions in the dimer of Alzheimer beta-amyloid domain [1-28] studied by mass spectrometry. Eur J Mass Spectrom (Chichester, Eng) 2004; 10(2):309-16.

[29] McLaurin J, Cecal R, Kierstead M E, Tian X, Phinney A L, Manea M, French J E, Lambermon M H L, Darabie A A, Brown M E, Janus C, Chishti M A, Horne P, Westaway D, Fraser P E, Mount H T J, Przybylski M, George-Hyslop P. Therapeutically effective antibodies against amyloid-beta peptide target amyloid-beta residues 4-10 and inhibit cytotoxicity and fibrillogenesis. Nature Medicine 2002 November; 8(11):1263-9.

[30] Morgan D, Diamond D M, Gottschall P E, Ugen K E, Dickey C, Hardy J, Duff K, Jantzen P, DiCarlo G, Wilcock D, Connor K, Hatcher J, Hope C, Gordon M, Arendash G W. A beta peptide vaccination prevents memory loss in an animal model of Alzheimer's disease. Nature 2000 December; 408(6815):982-5.

[31] Morgan D, Gitter B D. Evidence supporting a role for anti-Abeta antibodies in the treatment of Alzheimer's disease. Neurobiol Aging 2004 May; 25(5):605-8.

[32] Nicoll J A, Wilkinson D, Holmes C, Steart P, Markham H, Weller R O. Neuropathology of human Alzheimer disease after immunization with amyloid-beta peptide: a case report. Nat Med 2003 April; 9(4):448-52.

[33] Orgogozo J M, Gilman S, Dartigues J F, Laurent B, Puel M, Kirby L C, Jouanny P, Dubois B, Eisner L, Flitman S, Michel B F, Boada M, Frank A, Hock C. Subacute meningoencephalitis in a subset of patients with AD after Abeta42 immunization. Neurology 2003 July; 61(1):46-54.

[34] Savage M J, Trusko S P, Howland D S, Pinsker L R, Mistretta S, Reaume A G, Greenberg B D, Siman R, Scott R W. Turnover of amyloid beta-protein in mouse brain and acute reduction of its level by phorbol ester. J Neurosci 1998 March; 18(5):1743-52.

[35] Schenk D. Amyloid-beta immunotherapy for Alzheimer's disease: the end of the beginning. Nat Rev Neurosci 2002 October; 3(10):824-8.

[36] Schenk D, Barbour R, Dunn W, Gordon G, Grajeda H, Guido T, Hu K, Huang J, Johnson-Wood K, Khan K, Kholodenko D, Lee M, Liao Z, Lieberburg I, Motter R, Mutter L, Soriano F, Shopp G, Vasquez N, Vandevert C, Walker S, Wogulis M, Yednock T, Games D, Seubert P. Immunization with amyloid-beta attenuates Alzheimer-disease-like pathology in the PDAPP mouse [see comments]. Nature 1999 July; 400(6740):173-7.

[37] Schenk D, Hagen M, Seubert P. Current progress in beta-amyloid immunotherapy. Curr Opin Immunol 2004 October; 16(5):599-606.

[38] Seubert P, Vigo-Pelfrey C, Esch F, Lee M, Dovey H, Davis D, Sinha S, Schlossmacher M, Whaley J, Swindlehurst C,. Isolation and quantification of soluble Alzheimer's beta-peptide from biological fluids. Nature 1992 September; 359(6393):325-7.

[39] Solomon B. Immunological approach for the treatment of Alzheimer's disease. J Mol Neurosci 2003; 20(3):283-6.

[40] Stine W B, Jr., Dahlgren K N, Krafft G A, LaDu M J. In vitro characterization of conditions for amyloid-beta peptide oligomerization and fibrillogenesis. J Biol Chem 2003 March; 278(13):11612-22.

[41] Wang H W, Pasternak J F, Kuo H, Ristic H, Lambert M P, Chromy B, Viola K L, Klein W L, Stine W B, Krafft G A, Trommer B L. Soluble oligomers of beta amyloid (1-42) inhibit long-term potentiation but not long-term depression in rat dentate gyrus. Brain Res 2002 January; 924(2):133-40.

[42] Wang Q, Walsh D M, Rowan M J, Selkoe D J, Anwyl R. Block of long-term potentiation by naturally secreted and synthetic amyloid beta-peptide in hippocampal slices is mediated via activation of the kinases c-Jun N-terminal kinase, cyclin-dependent kinase 5, and p38 mitogen-activated protein kinase as well as metabotropic glutamate receptor type 5. J Neurosci 2004 March; 24(13):3370-8.

[43] Wang Z, Chang L, Klein W L, Thatcher G R, Venton D L. Per-6-substituted-per-6-deoxy beta-cyclodextrins inhibit the formation of beta-amyloid peptide derived soluble oligomers. J Med Chem 2004 June; 47(13):3329-33.

EXAMPLE 2

Anti-ADDL Monoclonal Antibodies (Development and Characterization)

Materials and Methods

Aβ derived diffusible ligand (ADDL) preparation: ADDLs were prepared according to previously published protocols (Lambert 1998, 2001; Klein 2002). Aβ1-42, from American Peptide Co. (Sunnyvale, Calif.) or California Peptide Research, Inc. (Napa, Calif.), was dissolved in hexafluoro-2-propanol (HFIP). To prepare ADDLs, an aliquot of Aβ1-42 was dissolved in neat DMSO to 5 mM, then added to cold F12 medium to 100 μM. This solution was incubated at 4° C. for 24 hours and centrifuged at 14,000×g for 10 min. The supernatant contains ADDLs.

Human fibril preparation: Samples obtained from frozen human cortex (NADC grant #AG 13854 and NADC Neuropathology Core) were homogenized in 20× cold F12 medium with protease inhibitors (Roche Complete®) for 1 min. The sample was then centrifuged at 10,000 g for 1 h at 4° C. After washing twice with F12, the pellet was resuspended in 2% SDS/F12 and incubated on ice for 30 min. The sample was then centrifuged at 220,000 g for 1 hr at 4 C. The pellet was then resuspended in cold F12 and sonicated for 1 min in 15 sec bursts. Protein was determined using Coomassie Plus kit (Pierce Biotechnology, Rockford, Ill.).

Hippocampal cultures: Cultures were prepared according to a modification of previously published procedures (Brewer, 1997; Stevens, 1996) from E18 embryos. Viable cells were counted and plated on coverslips coated with polylysine (200 µg/ml) at densities from $1.5 \times 10^4$-$10^6$ cells/cm2. The medium was changed by removing half and replacing with supplemented Neurobasal media.

Quantitative immunocytochemistry: Cultured hippcampal cells were incubated with 500 nM ADDLs for 1 hr at 37 C. ADDLs were then removed by washing and cells were fixed with 3.7% formaldehyde. Cells were incubated with 0.1% Triton X-100 in PBS-NGS (PBS with 10% normal goat serum) for 30 min, washed once, and incubated with the desired primary antibody(ies) (diluted in PBS-NGS) overnight at 4° C. Samples were then washed and incubated with the appropriate secondary(ies) [Alexa Fluor® 488 or 594 anti-mouse and anti-rabbit IgGs (Molecular Probes, Inc., Eugene, Oreg.)] for 2 h at 37° C. Coverslips were washed and mounted in ProLong anti-fade mounting medium (Molecular Probes, Inc., Eugene, Oreg.) and imaged using a Leica TCS SP2 confocal Scanner DMRXE7 microscope.

Western Blot: Samples were separated by native (4-20% Tris-HCl Ready Gel, BioRad) or SDS-PAGE (10-20% Tris Tricine Ready Gel, BioRad). Proteins were then transferred to nitrocellulose. Blots were blocked with 5% non-fat dry milk or 1% BSA in TBST (TBS with 0.1% Tween 20) overnight, incubated with primary antibody (ies) for 1.5 hr, washed, and incubated the HRP-conjugated secondary antibody (Amersham Biosciences Corp., Piscataway, N.J.) for 1 hr. After final washing, proteins were visualized with a West Femto chemiluminescence kit (Pierce Biotechnology, Rockford, Ill.) and an Image Station 440 CF (Kodak) or with film (Hyperfilm, Amersham Biosciences Corp., Piscataway, N.J.).

ELISA: Polyclonal anti-ADDLs IgG (M90/1; Bethyl Laboratories, Inc., Montgomery, Tex.) was plated at 0.25 mg/well on Immulon 3 Removawell strips (Dynatech Labs, VA, USA) for 2 h at RT and the wells blocked with 2% BSA in TBS. Samples diluted with 1% BSA in F12 were added to the wells, allowed to bind for 2 h at 4° C., and washed 3× with BSA/TBS at RT. Monoclonal antibodies diluted in BSA/TBS were incubated for 90 min at RT and detected with a Vectastain ABC kit to mouse IgG. The HRP label was visualized with BioRad peroxidase substrate and read at 405 nm on a Dynex MRX-TC microplate reader.

Isotyping: The Sigma Immunotype™ Kit with the Mouse Monoclonal Antibody Isotyping Reagents were used, following the manufacturer's directions (Sigma-Aldrich Co., St. Louis, Mo.).

Results and Discussion: see FIGS. 7-11 and Table 1 (below)

Conclusions: ADDLs elicit a strong immunogenic response in mice. Antibodies with four different binding profiles recognize denatured Aβ oligomers and are less selective with native Aβ oligomers. Antibodies can be further distinguished by their ability to recognize ADDLs that have been separated by size exclusion chromatography. Antibodies detect ADDLs bound to puncta along the neurites and soma of cultured cells. Puncta are ADDLs, and not attributable to Aβ monomer or large oligomeric species. Monoclonal antibodies show differential binding to ADDL-treated cultured cells. Monoclonal antibodies of several isotypes can be generated.

TABLE 1

Monoclonal Antibody Summary Table

| Clone Name | Isotype | Denatured Species Identified | | | Identified native ADDLs | Peak1 Peak 2 (ELISA) | Immuno-fluorescence |
|---|---|---|---|---|---|---|---|
| | | ADDLs | HMW ADDLs | Human fibrils | | | |
| 2A10 | IgG1 | Trimer, tetramer | Yes | Yes | High/low mw | 20 | Hot spots on processes, cell body |
| 2B4 | IgG2b | Trimer, tetramer | Yes | Yes | High/low mw | 63 | Cell body |
| 2D6 | | Tetramer | Yes | Yes | High/low mw | 19 | Cell body |
| 4C2 | IgG2a | No | Yes | Yes | High/low mw | 18 | Cell body |
| 4E2 | | Tetramer | Yes | Yes | High/low mw | 22 | Cell body |
| 5F10 | IgG2b | Trimer, tetramer | Yes | | High/low mw | 18 | Processes, no hot spots |
| 5G12 | IgM | Trimer, tetramer | Yes | Yes, plus three other bands | Only low mw | 5 | Cell body, processes |
| 6B7 | | No | Yes | Slight | No | 15 | NR |
| 6B11 | | No | Yes | Slight | No | 12 | Faint cell body |
| 11B4 | | Monomer, trimer, tetramer | Yes | | High/low mw | 15 | |
| 11B5 | IgG1 | Monomer, trimer, tetramer | Yes | | High/low mw | 22 | |
| 14A11 | | Monomer, trimer, tetramer | Yes | | High/low mw | 14 | |
| 15G6 | | Monomer, trimer, tetramer | Yes | | High/low mw | 16 | |
| 17G4 | | Monomer, trimer, tetramer | Yes | | High/low mw | 11 | |
| 20C2 | IgG1 | Monomer, trimer, tetramer | Yes | | High/low mw | 12 | |
| 3B7 | | Trimer, tetramer, 7-mer, 8-mer | No | No | No | −2 | |

Example 2 References

Hardy, J. & Selkoe, D. J. (2002) The amyloid hypothesis of Alzheimer's disease: progress and problems on the road to therapeutics. *Science* 297, 353-356.

Gong, Y., Viola, K. L. Lacor, P. N. Lambert, M. P., Finch, C. E., Krafft, G. A., & Klein, W. L. (2003) Alzheimer-affected brain: presence of oligomeric Aβ ligands (ADDLs) suggests a molecular basis for reversible memory loss. *Proc. Natl. Acad. Sci. USA* 100, 10417-10422.

Hock, C., Konietzko, U., Streffer, J. R., Tracy, J., Signorell, A., Mullet-Tillmanns, B. Lemke, U. Henke, K. Moritz, E., Carcia, M., Maddalena, A., Papassotiropoulos, A., and Nitsch, R. M. (2003) Antibodies against beta-amyloid slow cognitive decline in Alzheimer's disease. *Neuron* 38, 547-554.

Birmingham, K. and Frantz, S. (2002) Set back to Alzheimer vaccine studies. *Nat. Med.* 8, 199-200.

Klein, W. L. (2002) Aβ toxicity in Alzheimer's disease: globular oligomers (ADDLs) as new vaccine and drug targets. *Neurochem. Int.* 41, 345-352.

Lambert, M. P., Viola, K. L., Chromy, B. A., Chang, L., Morgan, T. E., Yu, J., Venton, D. L., Krafft, G. A., Finch, C. E. & Klein, W. L. (2001) Vaccination with soluble Abeta oligomers generates toxicity-neutralizing antibodies. *J. Neurochem.* 79, 595-605.

Dodart, J. C., Bales, K. R., Gannon, K. S., Greene, S. J., DeMattos, R. B., Mathis, C., DeLong, C. A., Wu, S., Wu, X., Holtzman, D. M., and Paul, S. M. (2002) Immunization reverses memory deficits without reducing brain Abeta burden in Alzheimer's disease. *Nat. Neurosci.* 5, 452-457.

Lambert, M. P., Barlow, A. K., Chromy, B. A., Edwards, C., Freed, R., Liosatos, M., Morgan, T. E., Rozovsky, I., Trommer, B., Viola, K. L., Wals, P., Zhang, C., Finch, C. E., Krafft, G. A. & Klein, W. L. (1998) Diffusible, nonfibrillar ligands derived from Abeta1-42 are potent central nervous system neurotoxins. *Proc. Natl. Acad. Sci. U. S. A* 95, 6448-6453.

Brewer, G. J. (1997) Isolation and culture of adult rat hippocampal neurons. *J. Neurosci. Methods* 71, 143-155.

Stevens, G. R., Zhang, C., Berg, M. M., Lambert, M. P., Barber, K., Cantallops, I., Routtenberg, A. & Klein, W. L. (1996) CNS neuronal focal adhesion kinase forms clusters that co-localize with vinculin. *J. Neurosci. Res.* 46, 445-455.

EXAMPLE 3

Anti-ADDL Monoclonal Antibodies as Diagnostic Reagents anti-ADDL antibodies, in particular monoclonal anti-ADDL antibodies specific for conformational epitopes found in ADDLs and not in amyloid monomers or fibrils, can be used in any diagnostic assay known to persons skilled in the art, including, but not limited to, protein assays; nucleic acid assays; pathological assays; Western blot assays; ELISA assays; RIA assays; dot blot assays; epidemiological assays; assays to detect compounds that inhibit the assembly of ADDLs; assays to detect compounds that inhibit the binding of ADDLs to their receptor(s); assays to detect compounds that prevent or treat Alzheimer's disease (AD), Down's syndrome, and mild cognitive impairment (MCI); assays to detect whether a patient or subject has Alzheimer's disease, Down's syndrome, and mild cognitive impairment; and the like (see e.g., Georganopoulou, D. G. et al. (2005) Nanoparticle-based detection in cerebral spinal fluid of a soluble pathogenic biomarker for Alzheimer's disease. Proc. Natl. Acad. Sci. USA 102(7):2273-76; International Patent Pub. No. WO 2005/003394; U.S. Pat. Nos. 6,872,554; 6,866,850; 6,815,175; 6,808,712; 6,787,523; 6,787,144; 6,710,226; 6,710,226; 6,703,015; 6,670,195; 6,582,945; 6,375,949; 6,194,163; 5,786,180; 5,716,619; 5,693,753; 5,693,478; 5,679,531; 5,270,165; U.S. Patent App. Pub. Nos. 2005/0142131; 2005/0129695; 2005/0119227; 2005/0090648; 2005/0053614; 2005/0048049; 2005/0037026; 2005/0031629; 2005/0019343; 2005/0019330; 2005/0013815; 2004/0265308; 2004/0234990; 2004/0228865; 2004/0219146; 2004/0197831; 2004/0192898; 2004/0181042; 2004/0175394; 2004/0170641; 2004/0166119; 2004/0157779; 2004/0081657; 2004/0052766; 2003/0235897; 2003/0157117; 2003/0086938; 2003/0073655; 2002/0182660; 2002/0150948; 2002/0136718; 2002/0102261; 2002/0086847; 2002/0009445; and the like).

Figure 12:
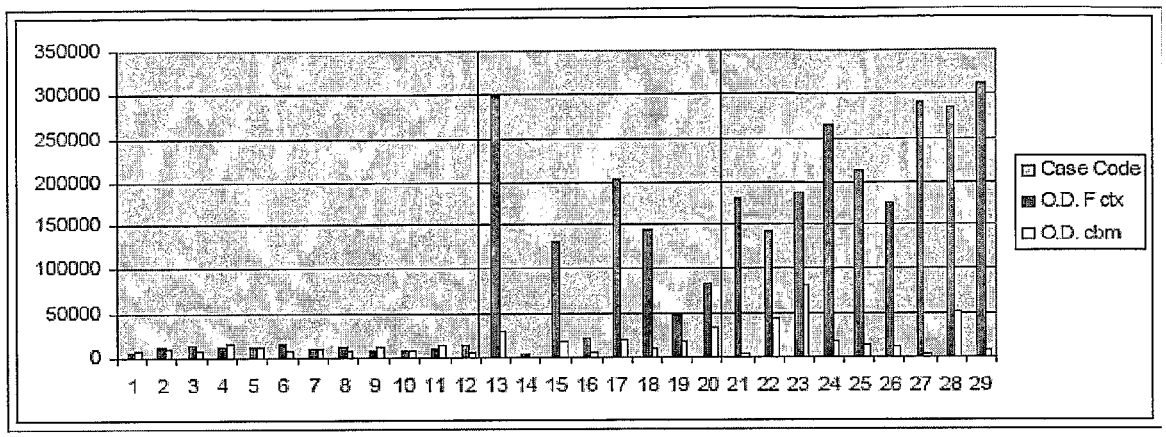
FIG. 12: Relative quantities of ADDLs in human brain extracts by dot blot immunoassay.
Figure 13B:
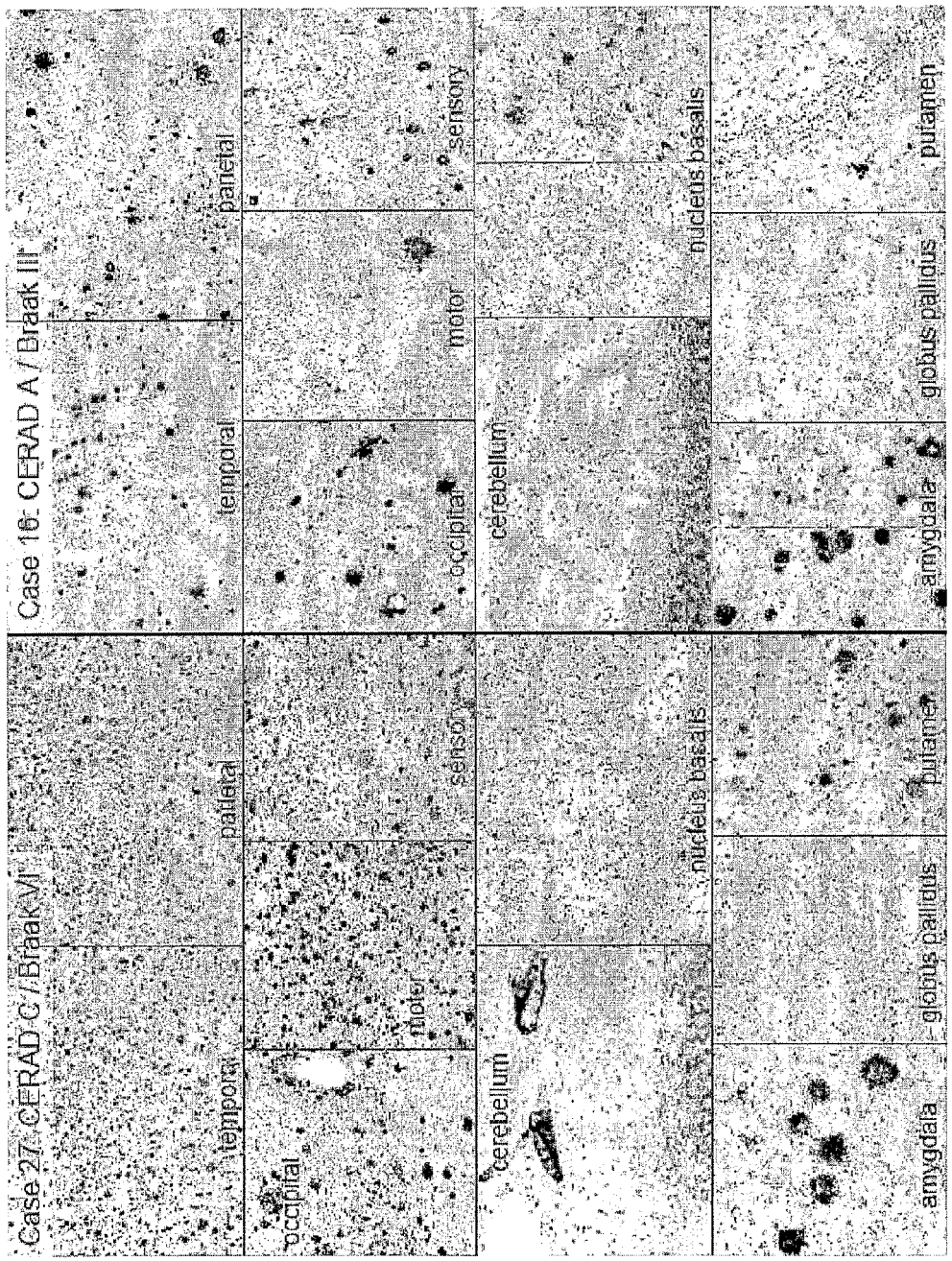
FIG. 13A-13-D: ADDL immunohistochemical (IHC) analyses of human brain sections. Regional distribution. 2 cases.
Figure 13C:
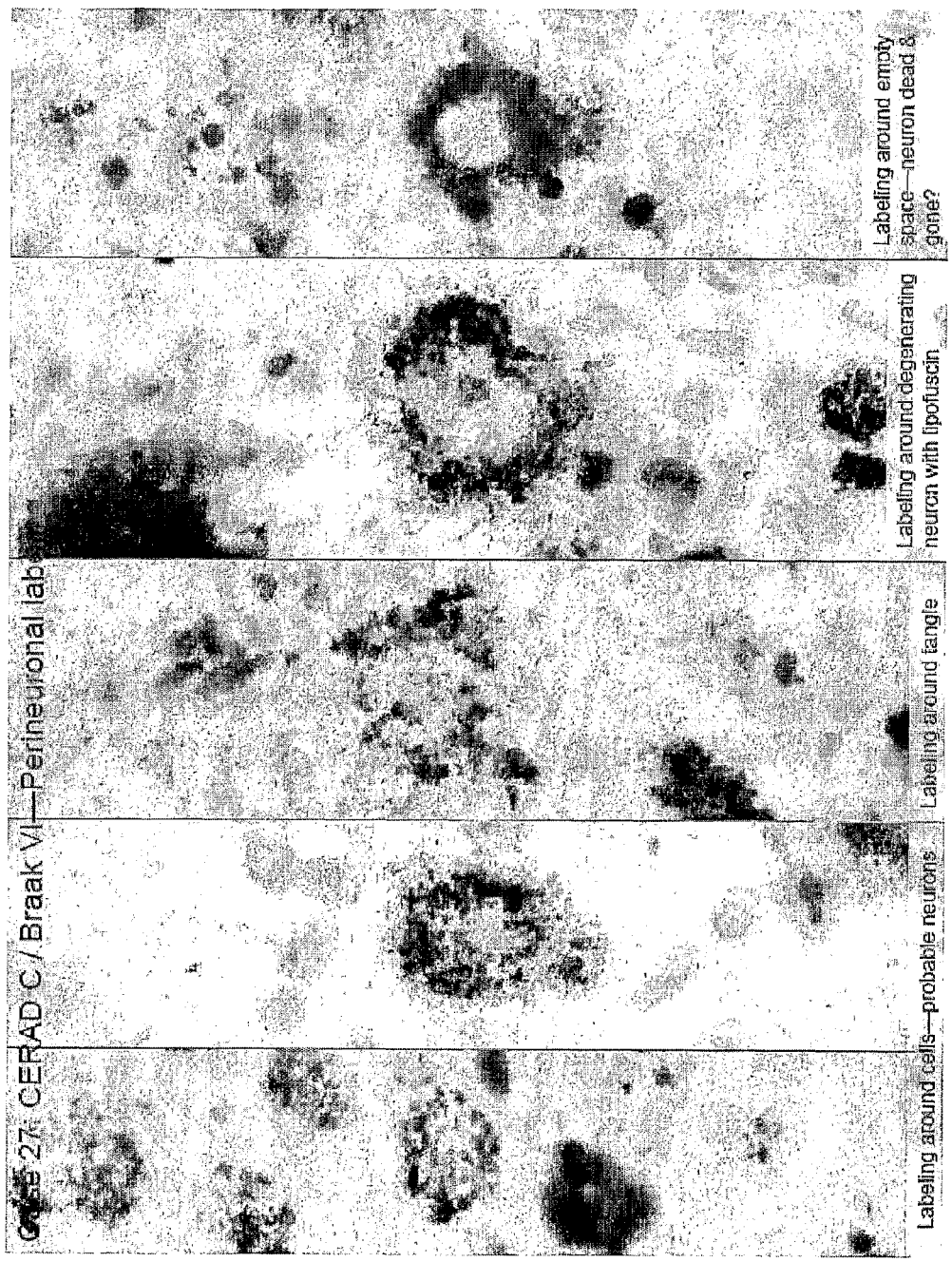
Figure 13D:
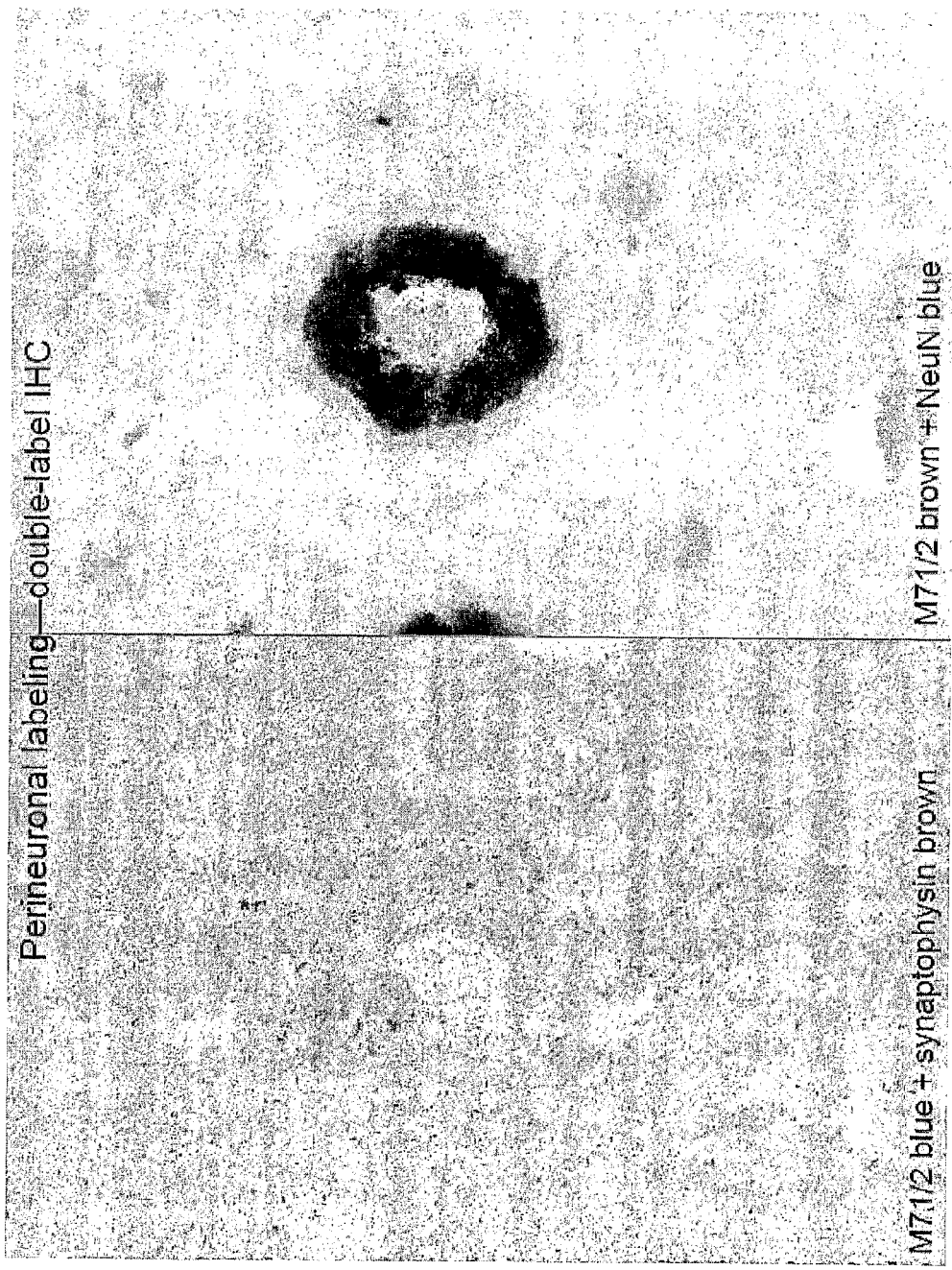

Monoclonal antibodies as disclosed herein can be used according to the methods, protocols, and procedures known to persons skilled in the art and disclosed herein to assay brain extracts for the presence of ADDLs (see e.g., FIG. 12). Such assays show that no or low pathology patients have very low detectable levels of ADDLs. Also, high pathology patients have variable levels of detectable ADDLs. Finally, such assays show that AD patients have consistently high levels of detectable ADDLs.

Monoclonal antibodies as disclosed herein can be used according to the methods, protocols, and procedures known to persons skilled in the art and disclosed herein to assay brain slice sections for the presence of ADDLs (see e.g., FIGS. 13A-13D). Such assays demonstrate that ADDLs are present in areas affected by AD pathology. ADDLs were not present in 2 controls, one with no AD pathology and one CERAD 0, Braak I. ADDLs were present in a "high" pathologic control sample—CERAD A, Braak III and in AD. Furthermore, there was more in an AD case than in the "high" pathologic control sample. Results of such assays show variable IHC patterns: peri-neuronal, diffuse plaque-like, neuritic plaque-like, amyloid angiopathy, Nbm peri-neuronal labeling—not an area that typically has plaques.

Figure 15:
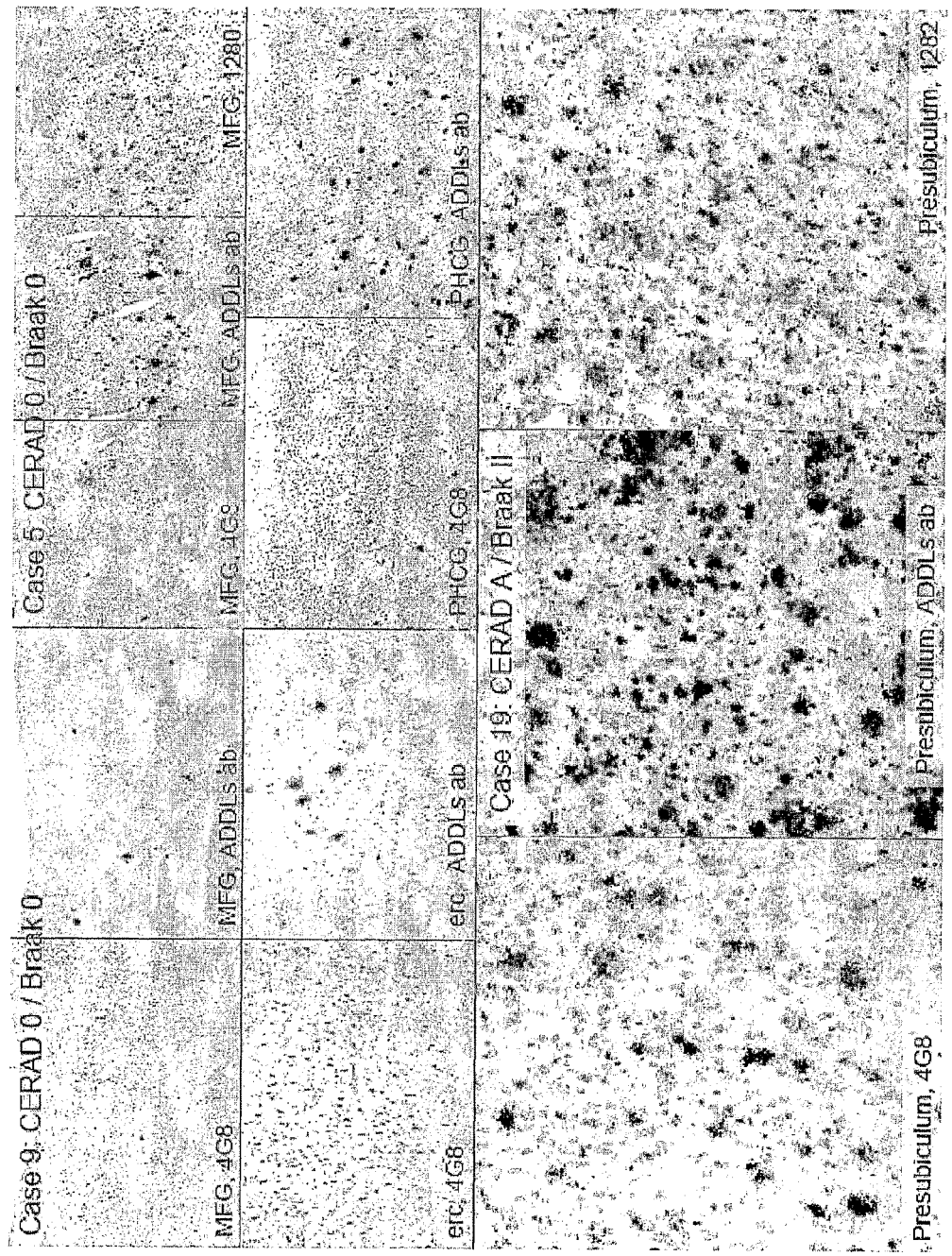
FIG. 15: ADDL immunohistochemical (IHC) analyses of human brain sections.

Immunohistochemical assays from 29 cases (see e.g., FIGS. 14, 15, & 16) show that the regions of the brain in which ADDLs can be found include, but are not limited to, Anterior Hippocampal section: Hippocampus, Subiculum, Presubiculum, Entorhinal cortex, Parahippocampal gyrus, Temporooccipital gyrus, Middle frontal gyrus. ADDLs can be evaluated semi-quantitatively for peri-neuronal, diffuse plaque-like, neuritic plaque-like deposits. With such assays, it is possible to compare selected cases to Abeta 4G8 and 1280 IHC (see e.g., FIG. 16). Furthermore, such assays allow one to investigate whether ADDL labeling correlates with cognitive status, whether ADDL labeling compares with measures of synapse loss; whether recruitment/activation of microglial cells correlates with transition to AD and/or MCI, and the like.

Figure 18:
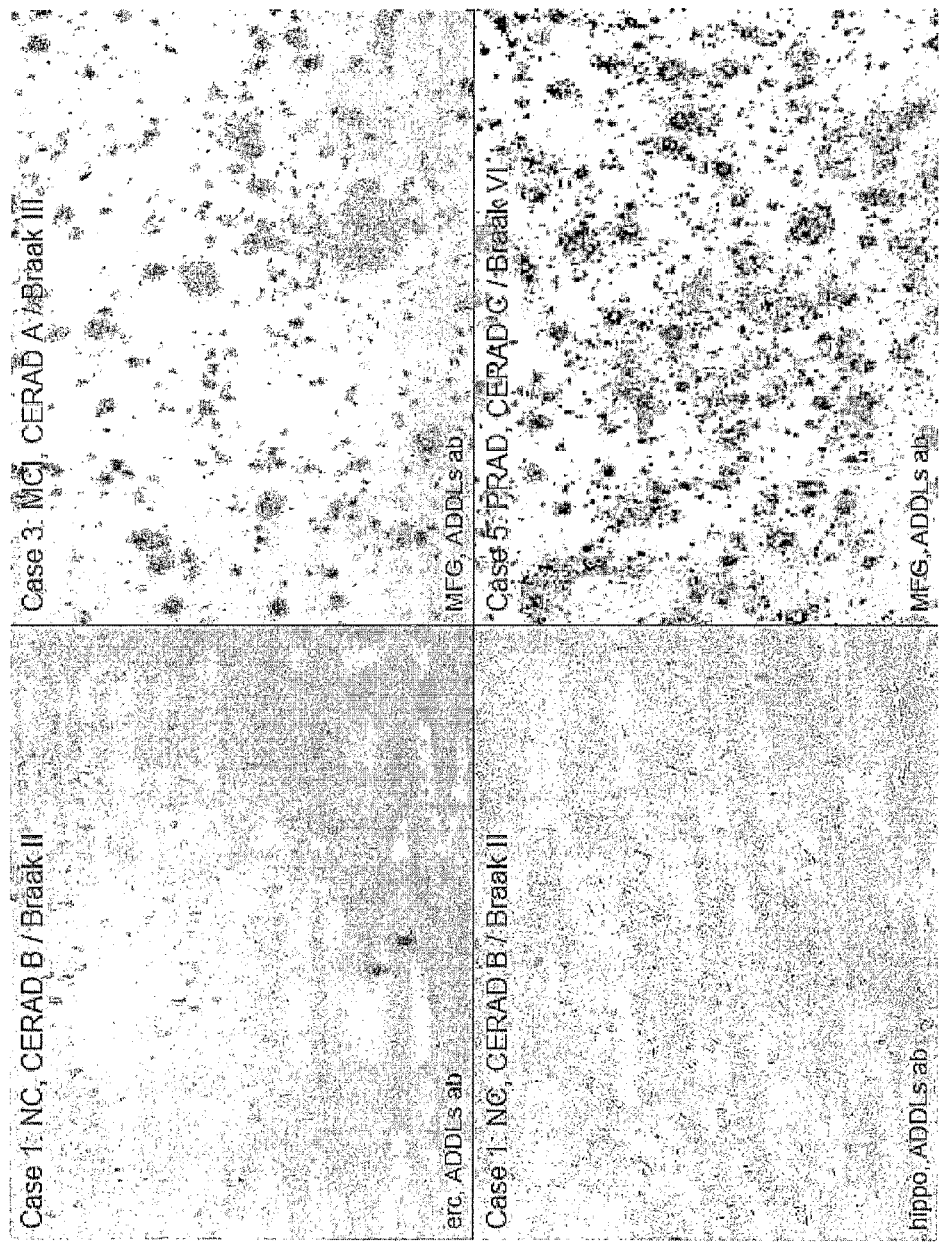
FIG. 18: ADDL IHC analyses with human brain sections on select cognitively evaluated cases.

Similar assays were performed with 6 cognitively evaluated cases, preliminary results of such assays are shown in FIGS. 17 and 18.

Such IHC assays provide information that can be summarized as follows: ADDL labeling correlates with AD pathology in regional distribution and density (exception: peri-neuronal nbm labeling), ADDL labeling correlates with cognitive status, and studies in human tissue correlate with in vitro cell culture and dot immunoblot assay studies.

Monoclonal antibodies as disclosed herein can be used according to the methods, protocols, and procedures known to persons skilled in the art and disclosed herein to assay CSF samples from normal and AD-diagnosed patients or subjects.

Figure 19:
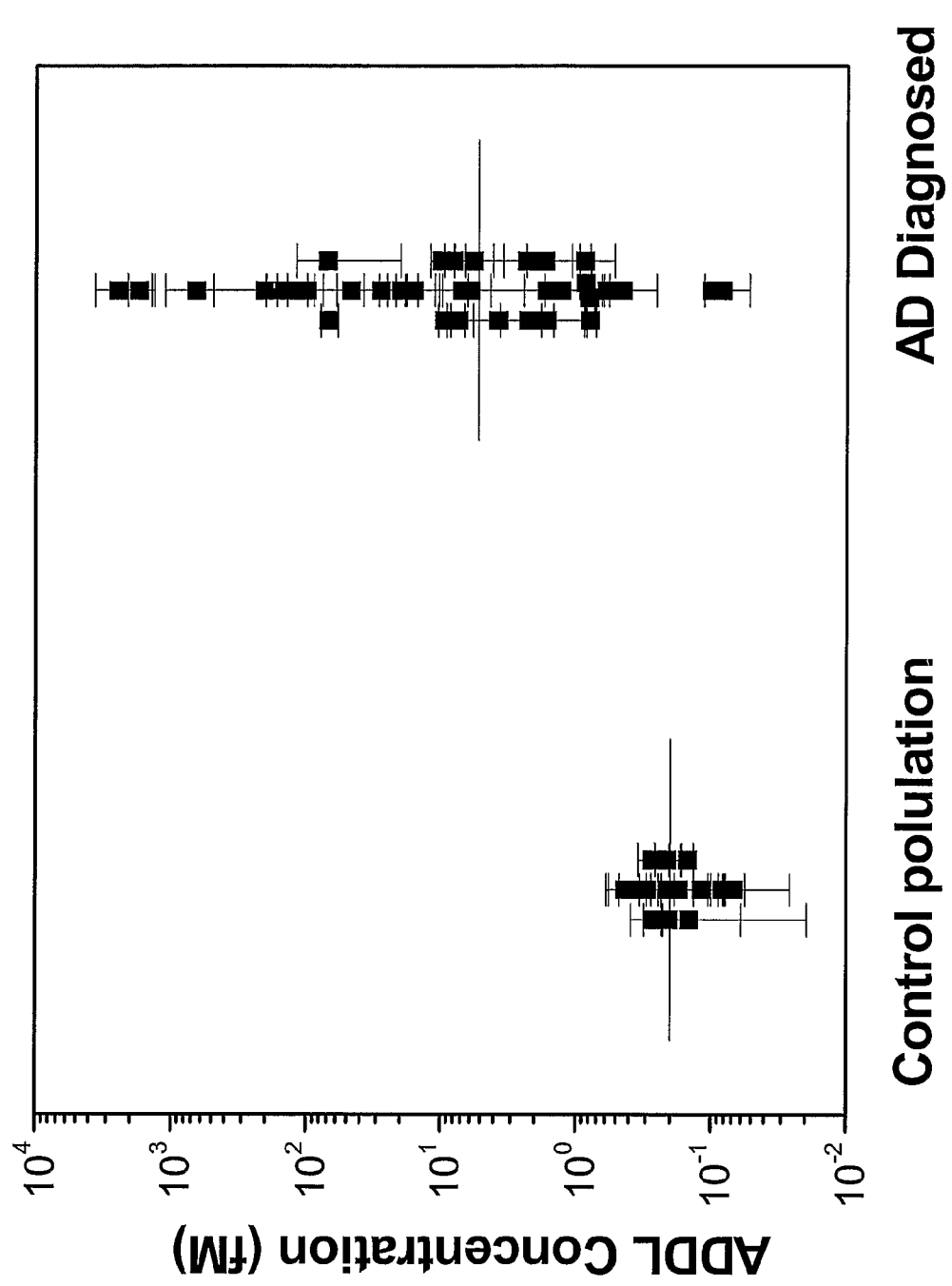
FIG. 19: Scatter plot analysis of data generated from the detection of barcode DNA released from a bio-barcode assay for multiple subjects, both normal and AD-diagnosed. (see e.g., Georganopoulou, D. G. et al. (2005) Nanoparticle-based detection in cerebral spinal fluid of a soluble pathogenic biomarker for Alzheimer's disease. Proc. Natl. Acad. Sci. USA 102(7):2273-76).

An exemplary assay using nanotechnology (see e.g., Georganopoulou, D. G. et al. (2005) Nanoparticle-based detection in cerebral spinal fluid of a soluble pathogenic biomarker for Alzheimer's disease. Proc. Natl. Acad. Sci. USA 102(7): 2273-76; International Patent Pub. No. WO 2005/003394; and the like) generates data as shown in FIG. 19, which can be used to assist a clinician in the diagnosis of AD. Elevated ADDL levels in CSF correlate with AD diagnosis and can be used as a marker of the disease (see also, related patent applications identified below, in particular, U.S. patent application Ser. Nos. 10/676,871 and 10/924,372 as well as International Patent App. No. PCT/US03/30930).

Monoclonal antibodies as disclosed herein can be used according to the methods, protocols, and procedures known to persons skilled in the art and disclosed herein in ELISA assays. Such assays show that ADDL binding to 26 DIV hippocampal cell cultures as detected by ELISA is concentration dependent.

Figure 20:
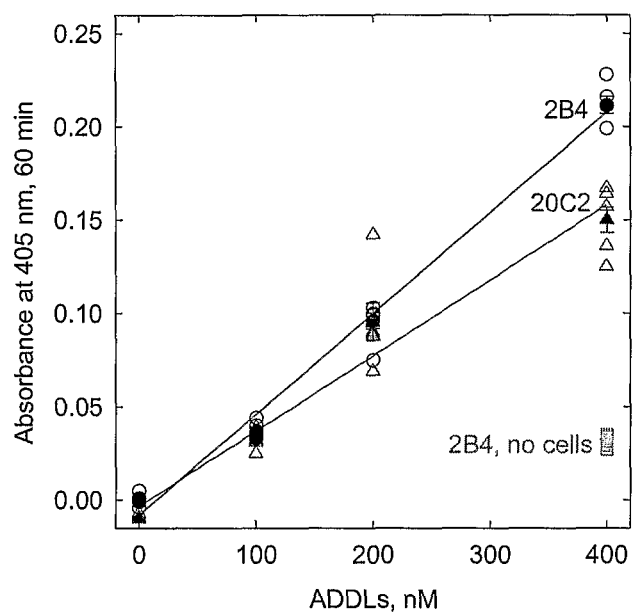
FIG. 20: ADDL-concentration dependent binding to 26 DIV hippocampal cell cultures detected by ELISA. Cultures were incubated with ADDLs for 1 hr at 37° C., labeled with monoclonal 2B4 or 20C2 antibody, and a HRP-linked anti-mouse IgG secondary antibody was used for detection. Individual readings (open symbols), the mean (solid symbols; n=6) and the SEM (bars) are plotted.

Referring to FIG. 20, hippocampal cells (26 DIV; plated 20,000 cells/well) were cultured in a 96-well plate. Non-cell control wells were plated with media. Cells were treated for 1 hr at 37° C. with 100 ml ADDLs diluted in culture media recovered from the growing cells. The wells were washed with 3×200 ml warm neurobasal media and 1×200 ml 1% BSA in TBS (20 mM Tris-HCl, pH 7.5, 0.8% NaCl) for 10 min each. Monoclonal antibodies were diluted to 2.5 mg/ml in BSA/TBS and incubated 100 ml/well for 1 hr at 37° C., followed by washing 4×10 min with 200 ml BSA/TBS. HRP-linked anti-mouse IgG (Amersham) was diluted 1:2500 in BSA/TBS and incubated 100 ml/well for 1 hr at RT, followed by washing with 4×200 ml BSA/TBS as above and rinsing with 3×200 ml TBS. Bio-Rad peroxidase substrate (100 ml) was added to each well, developed for 1 hr at RT, and read at 405 nm on a Dynex MRX Microplate Reader.

Monoclonal antibodies as disclosed herein can be used according to the methods, protocols, and procedures known to persons skilled in the art and disclosed herein in punctate binding ("hot spot") immunofluorescence assays (see e.g., FIG. 21, and analogous information in the related applications referred to below).

Figure 21:
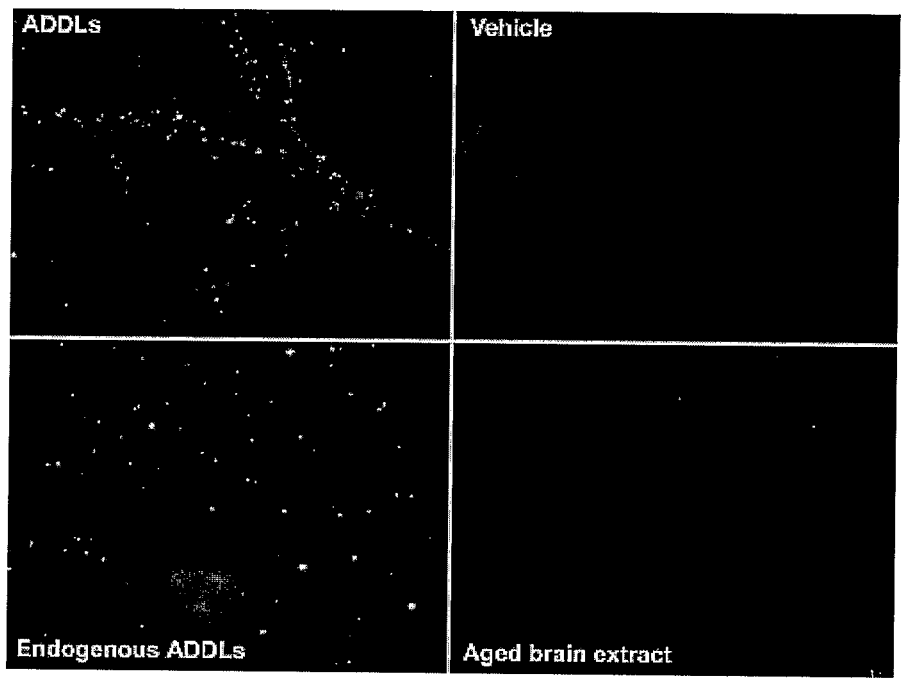
FIG. 21: Punctate binding ("hot spot") immunofluorescence assay using anti-ADDL monoclonal antibody 2B4. ADDLs prepared in vitro and endogenous ADDLs isolated from human brain extracts were added to hippocampal cells in culture and detected using the 2B4 monoclonal antibody.

Referring to FIG. 21, hippocampal cells were grown for 3 weeks on poly-lysine coated glass coverslips. The cells were treated with 100 μM ADDLs, equivalent volume of Vehicle, 0.5 mg (total protein) endogenous ADDLs (ADDLs extracted from AD brain), or 0.5 mg (total protein) aged matched control brain extract for 1 hour. Cells were fixed with 3.7% formaldehyde in PBS for a total of 15 minutes, rinsed with PBS, and immunolabeled with 2B4 antibody (1:500 dilution) followed by Alexa Fluor 488 anti-mouse secondary (Invitrogen). Cells were imaged using a Nikon optiphot inverted microscope and MetaMorph software (Universal Imaging). Images were processed using MetaMorph and Photoshop (Adobe). Typical punctate ADDL binding to hippocampal cells is detected using the 2B4 monoclonal antibody. Such assays are useful for a number of different analyses, including, but not limited to, detection and characterization of compounds that inhibit the binding of ADDLs to their receptor(s), detection and characterization of compounds that inhibit the assembly of ADDLs, and the like.

Related patents and patent applications include, but are not limited to, U.S. Pat. No. 6,218,506; International Patent App. No. PCT/US98/02426; International Patent Pub. No. WO 98/33815; U.S. patent application Ser. No. 09/369,236; International Patent App. No. PCT/US00/21458; U.S. patent application Ser. Nos. 09/745,057; 11/130,566; 10/166,856; International Patent App. No. PCT/US03/19640; U.S. patent application Ser. Nos. 10/676,871; 10/924,372; 11/100,212; 11/142,869; International Patent App. No. PCT/US03/30930; International Patent App. No. PCT/US05/17176; and the like.

All patents, patent applications, as well as any other scientific and technical writings mentioned herein are incorporated by reference to the extent that they are not contradictory.

The preceding description of preferred embodiments is presented for purposes of illustration and description, and is not necessarily exhaustive nor intended to limit the claimed invention to the precise form(s) disclosed. The description was selected to best explain the principles of the invention and practical application of these principles to enable others skilled in the art to best utilize the claimed invention in various embodiments and with various modifications as are suited to the particular use contemplated. The scope of the claimed invention is not to be limited by the specification, but defined by the claims herein.

We claim:

1. A method for neutralizing the binding of soluble Abeta oligomers to cells comprising contacting soluble Abeta oligomers with a monoclonal antibody that selectively binds soluble 12-24 oligomers of Abeta 1-42 over trimers and tetramers of Abeta 1-42, and inhibits binding of soluble Abeta oligomers to cells, thereby neutralizing the binding of soluble Abeta oligomers to cells.

* * * * *